United States Patent
Sundaresan et al.

(10) Patent No.: US 7,109,395 B2
(45) Date of Patent: Sep. 19, 2006

(54) DEHISCENCE GENE AND METHODS FOR REGULATING DEHISCENCE

(75) Inventors: Venkatesan Sundaresan, Davis, CA (US); Sarojam Rajani, Davis, CA (US)

(73) Assignee: Temasek Life Sciences Laboratory Limited, Singapore (SG)

( * ) Notice: Subject to any disclaimer, the term of this patent is extended or adjusted under 35 U.S.C. 154(b) by 114 days.

(21) Appl. No.: 10/203,351

(22) PCT Filed: Feb. 1, 2001

(86) PCT No.: PCT/SG01/00017

§ 371 (c)(1),
(2), (4) Date: Jan. 15, 2003

(87) PCT Pub. No.: WO01/59122

PCT Pub. Date: Aug. 16, 2001

(65) Prior Publication Data

US 2003/0208787 A1    Nov. 6, 2003

(30) Foreign Application Priority Data

Feb. 11, 2000 (SG) ............................... SG00/00022

(51) Int. Cl.
*C12N 15/09* (2006.01)
*C12N 15/29* (2006.01)
*C12N 15/82* (2006.01)
*A01H 5/00* (2006.01)

(52) U.S. Cl. ................... 800/290; 800/278; 800/298; 800/287; 435/69.1; 435/468; 536/23.6

(58) Field of Classification Search ................ 800/290, 800/278, 298, 295, 287; 435/468, 430, 69.1; 536/23.6
See application file for complete search history.

(56) References Cited

FOREIGN PATENT DOCUMENTS

| | | | |
|---|---|---|---|
| EP | 1 033 405 A2 | 9/2000 | |
| WO | WO 94/23043 | * 10/1994 | |
| WO | WO 99/00502 A1 | 1/1999 | |

OTHER PUBLICATIONS

Lazar et al. Molecular and Cellular Biology, Mar. 1988, vol. 8, No. 3, pp. 1247-1252.*
Broun et al. Science, Nov. 13, 1998, vol. 282, pp. 1315-1317.*
Bird et al, Biology and Genetic Review, vol. 9, pp. 207-227 (1991).*
Sandler et al. Plant Molecular Biology, vol. 11, pp. 301-310 (1988).*
Napoli et al. The Plant Cell, vol. 2, pp. 279-289, 1990.*
Y. Nakamura et al., "*Arabidopsis thaliana* genomic DNA, chromosome 5, TAC clone:K21H1," Dec. 14, 1998, Database EMBL (online) Accession No. AB02020742, XP-002149439.
S. Sato et al., "Structural Analysis of *Arabidopsis thaliana* Chromosome 5. X. Sequence Features of the Regions of 3,076,755 bp Covered by Sixty P1 and TAC Clones," DNA Research 7:31-63, 2000.
S.D. Rounsley et al., "T19M21TF TAMU *Arabidopsis thaliana* genomic clone T19M21, genomic survey sequence," Nov. 21, 1997, Database EMBL (online) Accession No. B61971, XP-002149440.
J. Alcala et al., "EST243195 tomato ovary, TAMU *Lycopersicon esculentum* cDNA clone cLED1H9, mRNA sequence," Mar. 17, 1999, Database EMBL (online) Accession No. A1484932.
Gu et al., "The Fruitfull Mads-box gene mediates cell differentiation during *Arabidopsis* fruit development," Development 125(8):1509-1517, Apr. 1, 1998.
S. Parinov et al., "Analysis of Flanking Sequences from Dissociation Insertion Lines: A Database for Reverse Genetics in *Arabidopsis*," The Plant Cell 11:2263-2270, Dec. 1999.
V. Sundaresan et al., "Patterns of gene action in plant development revealed by enhancer trap and gene trap transposable elements," Genes & Development 9(14):1797-1810, 1995.

* cited by examiner

*Primary Examiner*—Medina A. Ibrahim
(74) *Attorney, Agent, or Firm*—Rothwell, Figg, Ernst & Manbeck, P.C.

(57) ABSTRACT

The present invention relates to isolated DNA sequences from Arabidopsis encoding proteins for regulating dehiscence of mature fruits and transgenic plants with delayed fruit dehiscence. The invention also relates to methods of preventing dispersal of seeds through the process of dehiscence (pod shattering) by transforming plants with DNA sequences encoding proteins that cause an indehiscent phenotype.

10 Claims, 8 Drawing Sheets

```
AGAGAGAGAGAGAGAGAGAGAGATGGGTGATTCTGACGTCGGTGATCGTCTTCCCCCTCC  60
                        M  G  D  S  D  V  G  D  R  L  P  P  P

ATCTTCTTCCGACGAACTCTCGAGCTTTCTCCGACAGATTCTTTCCCGTACTCCTACAGC 120
 S  S  S  D  E  L  S  S  F  L  R  Q  I  L  S  R  T  P  T  A

TCAACCTTCTTCACCACCGAAGAGTACTAATGTTTCCTCCGCTGAGACCTTCTTCCCTTC 180
 Q  P  S  S  P  P  K  S  T  N  V  S  S  A  E  T  F  F  P  S

CGTTTCCGGCGGAGCTGTTTCTTCCGTCGGTTATGGAGTCTCTGAAACTGGCCAAGACAA 240
 V  S  G  G  A  V  S  S  V  G  Y  G  V  S  E  T  G  Q  D  K

ATATGCTTTCGAACACAAGAGAAGTGGAGCTAAACAGAGAAATTCGTTGAAGAGAAACAT 300
 Y  A  F  E  H  K  R  S  G  A  K  Q  R  N  S  L  K  R  N  I

TGATGCTCAATTCCACAACTTGTCTGAAAAGAAGAGGAGGAGCAAGATCAACGAGAAAAT 360
 D  A  Q  F  H  N  L  S  E  K  K  R  R  S  K  I  N  E  K  M

GAAAGCTTTGCAGAAACTCATTCCCAATTCCAACAAGACTGATAAAGCCTCAATGCTTGA 420
 K  A  L  Q  K  L  I  P  N  S  N  K  T  D  K  A  S  M  L  D

TGAAGCTATAGAATATCTGAAGCAGCTTCAACTTCAAGTCCAGACTTTAGCCGTTATGAA 480
 E  A  I  E  Y  L  K  Q  L  Q  L  Q  V  Q  T  L  A  V  M  N

TGGTTTAGGCTTAAACCCTATGCGATTACCACAGGTTCCACCTCCAACTCATACAAGGAT 540
 G  L  G  L  N  P  M  R  L  P  Q  V  P  P  P  T  H  T  R  I

CAATGAGACCTTAGAGCAAGACCTGAACCTAGAGACTCTTCTCGCTGCTCCTCACTCGCT 600
 N  E  T  L  E  Q  D  L  N  L  E  T  L  L  A  A  P  H  S  L

GGAACCAGCTAAAACAAGTCAAGGAATGTGCTTTTCCACAGCCACTCTGCTTTGAAGATA 660
 E  P  A  K  T  S  Q  G  M  C  F  S  T  A  T  L  L

ACATTCAGACAATGATGATGATCGGAATTCCTCTAGTACCTGCCAGACAGGAGTGAACAA 720

TGTTTTGAGTTTTAGCATTGGCCAGATTTCTATGTTCAGTTATAGTTATGCTAATAAGCT 780

TTAGGAGTGAACAAAATCTGAGTAGTTTGATTATAATGATGTCTGAAGCAGATTATATAT 840

AAAAGACTAATTTACTTACATATGAGATGATTATTACAACTATCAAATGACTATGTCTGT 900

GAGTTGCATCCAAAAAAAAAAAAAAAAAAAA                              931
```

FIG. 4A

```
rd22BPI    1  MTDYRLQPTMNLWTTDDNASMMEAFMSSSDISTLWPP-----ASTTTTTATTETTPTPAM
PG1        1  MTEYRSPPTMNLWT-DDNASVMEAFMSSSDFSSLWLPTPQSAASTTTPGADTARALPPPP
Lc         1  ----------------------------------------------MALSASRVQQA--
B-Peru     1  ----------------------------------------------MALSASPAQ----
SGT10166   1  ------------------------------------------------------------ rd22BPI    56  EIPAQAGFNQETLQQRLQALIEGTHEGWTYAIPWQPSYDFSG-ASVLGWGDGYIKGEEDK
PG1        60  PSQSQSLFNQETLQQRLQETLQQRLQTLIEGAEESNTYALWQSSYDYSSTSLLGWGDYIKGEEDK
Lc         12  EELLQRPAERQLMRSQLAAARAR--SINWSYALEWSISDTQ-P--GVETWTBGFYNG-EVK
B-Peru     10  EELLQ-PAGRP-LRKQLAAARAR--SINWSYALEWSISTQRP--RVLTWTDGFYNG-EVK
SGT10166   1  ------------------------------------------------------------ rd22BPI    115  ANPRRRGSSPPFSTPADQEYRKKVLREL-NSLISG-------------GVAPSD
PG1        120  G-----KGK--APKEMSSAEQDHRKKVLREL-NSLISG-------------PFR-SA
Lc         66  T---RKISNSVELTSDQLVMQRSDQLRELYEALLSGE-----------GDRRAAPARPAG
B-Peru     63  T---RKISHSVELTADQLLMQRSEQLRELYEALRSGE-----------CDRRG-ARPVG
SGT10166   1  ------------------------------------------------------------ rd22BPI    155  DAVDEVTDTEWFFLVSMTQSFACGAGLAGKAFATGNAVWVSGSDQLSGSGCERAKQGGV
PG1        155  DDVDEVSDTEWFFEVSMTQSMTQSLSGGSLPGQAFLNSSPVWVAGADRLSDSTSERARQGQV
Lc         112  SLSPEDLGDTEWYVIVSMTYARRECQGLPGRSFASDEHVWICNAHLAGSKAFPRALLAKS
B-Peru     107  SLSPEDLGDTEWYVICMTVAELPGQGLPGRSSASNEHVWLCNAHLAGSKDFPRALLAKS
SGT10166   1  ------------------------------------------------------------ rd22BPI    215  FGMHTIACTPSANGVVEVGSTEPHRQSSDLINKVRILFNEDGGDGDLSGLNWNLDPDQGE
PG1        215  FGVQTLVCTPSANGVVEVGSTEPHRQSSDLINKVRILFNEDGGDGDLSGLNWNLDPDQGE
                                                                   MKKVRDLFNFNNPD---AGFWPLN--QGE
Lc         172  ASIQSLCIPVMGGVLELGTIDTVPEAPDLVS--RATAAFWEPQCP---SSSPSGRA
B-Peru     167  ASIQLIVCIRLMGGWLELGTIDKVPEDPDLVS--RATVAFWEPQCPTYSKEPSSNPS--A
SGT10166   1  ------------------------------------------------------------
```

FIG. 4B-1

```
rd22BPI   275 NDPS-MWINDPIGTPGSNEPGNGAPSSSQLFSKS-IQFENGSSTITENDLDPTPSPV
PG1       269 NDPSSLWLNPSSSIEIKDTSNAVALVSANASLSKT-MPFETPGSSTLTETP----SAAA
Lc        224 NETGEAAADGTFAFELDHNGMDDIEAMTAAGG-HGQEELRLREABALSDD---ASLE
B-Peru    223 YETGEAAY---IVVLEDLDHN--AMDMETVTAAAGRHGTGQELG--EVBSPSN---ASLE
SGT10166    1 -----------------MGDSDVGDRLPP-PSSSDELS----------------SFLR rd22BPI   333 HSQTQNPKENNTFSRELNFSDVKFYFSEPRSGEILNFGDEGKRSSGNEDPSSYSGQEFE
PG1       323 AAHVPNBKNQGFFPRELNESNS---LKPESGEILSFG-ESKKSYNG--SYFPGVAAEE
Lc        281 HITKELEEFY-SLCDEMDLQALP--LPLEDGWTVDASNFEVPCSSPQBAPPPVDRATANV
B-Peru    273 HITKGLDEFY-SLCEEMDVQ------PLEDAWIMDGSNFEVPSS------ALPVD----
SGT10166   25 QILSRTDTAQ-------------PSS----PPKSTNVSSAETFFPS------------ rd22BPI   393 -NKRKRSMVLN---EDKIVLSF-----------GDKTAGESDHSDLEA-------S
PG1       376 TNKKRRSEASRSSIDDGMLSETSGVIIPASNIKSGAVAGGASGGDSENSDLEA------S
Lc        338 AADASRAPYG---SRATSF---------------MAWTRSSQQSSCBDDAAPAAVVP
B-Peru    315 ---GSSAPADG--SRATSE---------------VVWTRSS-HSCSGEAA-----VP
SGT10166   54 -------GAVSS-----NSG--------------VGYGVSETGQDK---------- rd22BPI   426 VVKEVA--VE--KRPKKRGRKPA---NG-----REE---PLNHVEAERQRREKLNQ
PG1       431 VVKEADSRVVEPEKRPRKRGRKPG--NG-----REE---PLNHVEAERQRREKLNQ
Lc        378 AIEEPQR-LLK-KVVAGGGAWES--CGG--ATGAAQEMSGTGTKNHVMSERKRREKLNE
B-Peru    346 VIEEPQK-LLK-KALAGGGAWANTNCGGGGTTVTAQEN--GAKNHVMSERKRREKLNE
SGT10166   74 YAFEHKR-------SGAKQRNSLKR------------MID----AQFENLSEKKRSKINE Basic    -><-    H1
```

FIG. 4B-2

```
rd22BPI    467  RFYALRAVVPNVSKMDKASLIGDAIAYINEKSKVVKTIESEKLQ--------------I
PG1        477  RFYALRAVVPNVSKMDKASLIGDAISYINEKSKLSELESEKGE--------------L
Lc         431  MELVLKSLEPSTHRVNKASLAETIAYLKELQRRVQEESSREPASRPSETTRLITRPS
B-Peru     400  MELVLKSLVPSIHKVDKASILAETIAYLKELQRRVQELESRRQ--------------
SGT10166   112  KMKALQKLIPNSNKTDKASMLDEAILEYLKQLQLQVQTLAVMNG-------------
                  -><-     loop     -><-        H2         -> rd22BPI    512  KNQLEEVK---LELAG-------RKASPSGG----DMSSSCSSIKPVGMEIEVKIIG-WDAMIRVE
PG1        522  EKQLELVKKELELAT-------KSPSPPPGPPPSNKEAKETTSKLIDLELEVKIIG-WDAMIRIQ
Lc         491  RGNNESVRKEVCAGS----KRKSPELGR---DDVERPPVLTMDAGTSNVTVTVSDKDVLLEVQ
B-Peru     443  -GGSGCVSKKVCNGSNSKRKSPEFAG---GAKEHPWVLPMD-GTSNVTVTVSDTNVLLEVQ
SGT10166   155  LGLNPMRLPQVPPPI-------HTRIN-----ETLEQDLNLETLLAAPHSLEPAK--TSQGM rd22BPI    563  SSKRNHPAARLMSALMDEEEWNHASMSVVNDLM-IQQATVKMGFRIYTQDQLRASLISK
PG1        579  CSKKNHPAARLMAARELDEDVNHASVSVVNDLM-IQQATVNMGNRFYTQEQLRSARSSK
Lc         547  CRWEELEMTRVFDAIKSHHDVLSVQASAPDGFMGLKIRAQFAGSGAVVPWMISEALRKA
B-Peru     499  CRWEKLEMTRVFDAIKSHLDALSVQASAPDGFMRLKIGAQFAGSGAVVPGMISQSLRKA
SGT10166   203  CFSTATLL------- rd22BPI    622  IG----
PG1        638  IGNAL
Lc         607  IGKR-
B-Peru     559  IGKR-
SGT10166        -----
```

FIG. 4B-3

(1) Wildtype ALC:    GAAGAGGAGGA                              GCAAGATCAAC

3'-DsG-5'
                                         ▽
(2) Ds tagged alc:   GAAGAGGAGGA CCT         AGAGGA           GCAAGATCAAC (3) Revertant:       GAAGAGGAGGA CCT TAAGGA                   GCAAGATCAAC (4) alc10            GAGGAGGAGGA CCT CTGAGGA                  GCAAGATCAAC

FIG. 5

SEQUENCE LISTING

<160> NUMBER OF SEQ ID NOS: 16

<210> SEQ ID NO 1
<211> LENGTH: 931
<212> TYPE: DNA
<213> ORGANISM: Arabidopsis thaliana
<220> FEATURE:
<221> NAME/KEY: CDS
<222> LOCATION: (23)..(652)

<400> SEQUENCE: 1

```
agagagagag agagagagag ag atg ggt gat tct gac gtc ggt gat cgt ctt      52
                         Met Gly Asp Ser Asp Val Gly Asp Arg Leu
                          1               5                  10 ccc cct cca tct tct tcc gac gaa ctc tcg agc ttt ctc cga cag att      100
Pro Pro Pro Ser Ser Ser Asp Glu Leu Ser Ser Phe Leu Arg Gln Ile
                 15                  20                  25 ctt tcc cgt act cct aca gct caa cct tct tca cca ccg aag agt act      148
Leu Ser Arg Thr Pro Thr Ala Gln Pro Ser Ser Pro Pro Lys Ser Thr
         30                  35                  40 aat gtt tcc tcc gct gag acc ttc ttc cct tcc gtt tcc ggc gga gct      196
Asn Val Ser Ser Ala Glu Thr Phe Phe Pro Ser Val Ser Gly Gly Ala
     45                  50                  55 gtt tct tcc gtc ggt tat gga gtc tct gaa act ggc caa gac aaa tat      244
Val Ser Ser Val Gly Tyr Gly Val Ser Glu Thr Gly Gln Asp Lys Tyr
 60                  65                  70 gct ttc gaa cac aag aga agt gga gct aaa cag aga aat tcg ttg aag      292
Ala Phe Glu His Lys Arg Ser Gly Ala Lys Gln Arg Asn Ser Leu Lys
75                  80                  85                  90 aga aac att gat gct caa ttc cac aac ttg tct gaa aag aag agg agg      340
Arg Asn Ile Asp Ala Gln Phe His Asn Leu Ser Glu Lys Lys Arg Arg
                 95                 100                 105 agc aag atc aac gag aaa atg aaa gct ttg cag aaa ctc att ccc aat      388
Ser Lys Ile Asn Glu Lys Met Lys Ala Leu Gln Lys Leu Ile Pro Asn
             110                 115                 120 tcc aac aag act gat aaa gcc tca atg ctt gat gaa gct ata gaa tat      436
Ser Asn Lys Thr Asp Lys Ala Ser Met Leu Asp Glu Ala Ile Glu Tyr
         125                 130                 135 ctg aag cag ctt caa ctt caa gtc cag act tta gcc gtt atg aat ggt      484
Leu Lys Gln Leu Gln Leu Gln Val Gln Thr Leu Ala Val Met Asn Gly
     140                 145                 150 tta ggc tta aac cct atg cga tta cca cag gtt cca cct cca act cat      532
Leu Gly Leu Asn Pro Met Arg Leu Pro Gln Val Pro Pro Pro Thr His
155                 160                 165                 170 aca agg atc aat gag acc tta gag caa gac ctg aac cta gag act ctt      580
Thr Arg Ile Asn Glu Thr Leu Glu Gln Asp Leu Asn Leu Glu Thr Leu
                 175                 180                 185 ctc gct gct cct cac tcg ctg gaa cca gct aaa aca agt caa gga atg      628
Leu Ala Ala Pro His Ser Leu Glu Pro Ala Lys Thr Ser Gln Gly Met
             190                 195                 200 tgc ttt tcc aca gcc act ctg ctt tgaagataac attcagacaa tgatgatgat     682
Cys Phe Ser Thr Ala Thr Leu Leu
         205                 210 cggaattcct ctagtacctg ccagacagga gtgaacaatg ttttgagttt tagcattggc   742
cagatttcta tgttcagtta tagttatgct aataagcttt aggagtgaac aaaatctgag   802
tagtttgatt ataatgatgt ctgaagcaga ttatatataa aagactaatt tacttacata   862
tgagatgatt attacaacta tcaaatgact atgtctgtga gttgcatcca aaaaaaaaa    922
``` aaaaaaaaa                                                            931

<210> SEQ ID NO 2
<211> LENGTH: 210
<212> TYPE: PRT
<213> ORGANISM: Arabidopsis thaliana

<400> SEQUENCE: 2

Met Gly Asp Ser Asp Val Gly Asp Arg Leu Pro Pro Ser Ser Ser
1               5                   10                  15

Asp Glu Leu Ser Ser Phe Leu Arg Gln Ile Leu Ser Arg Thr Pro Thr
            20                  25                  30

Ala Gln Pro Ser Ser Pro Pro Lys Ser Thr Asn Val Ser Ser Ala Glu
        35                  40                  45

Thr Phe Phe Pro Ser Val Ser Gly Gly Ala Val Ser Ser Val Gly Tyr
    50                  55                  60

Gly Val Ser Glu Thr Gly Gln Asp Lys Tyr Ala Phe Glu His Lys Arg
65              70                  75                  80

Ser Gly Ala Lys Gln Arg Asn Ser Leu Lys Arg Asn Ile Asp Ala Gln
            85                  90                  95

Phe His Asn Leu Ser Glu Lys Lys Arg Arg Ser Lys Ile Asn Glu Lys
            100                 105                 110

Met Lys Ala Leu Gln Lys Leu Ile Pro Asn Ser Asn Lys Thr Asp Lys
            115                 120                 125

Ala Ser Met Leu Asp Glu Ala Ile Glu Tyr Leu Lys Gln Leu Gln Leu
130                 135                 140

Gln Val Gln Thr Leu Ala Val Met Asn Gly Leu Gly Leu Asn Pro Met
145                 150                 155                 160

Arg Leu Pro Gln Val Pro Pro Pro Thr His Thr Arg Ile Asn Glu Thr
                165                 170                 175

Leu Glu Gln Asp Leu Asn Leu Glu Thr Leu Leu Ala Ala Pro His Ser
            180                 185                 190

Leu Glu Pro Ala Lys Thr Ser Gln Gly Met Cys Phe Ser Thr Ala Thr
            195                 200                 205

Leu Leu
    210

<210> SEQ ID NO 3
<211> LENGTH: 2640
<212> TYPE: DNA
<213> ORGANISM: Arabidopsis thaliana
<220> FEATURE:
<221> NAME/KEY: exon
<222> LOCATION: (1007)..(1243)
<223> OTHER INFORMATION: Exon 1 not including sequence before the
      translation start site.
<220> FEATURE:
<221> NAME/KEY: Intron
<222> LOCATION: (1244)..(1355)
<223> OTHER INFORMATION: Intron 1.
<220> FEATURE:
<221> NAME/KEY: exon
<222> LOCATION: (1356)..(1427)
<223> OTHER INFORMATION: Exon 2.
<220> FEATURE:
<221> NAME/KEY: Intron
<222> LOCATION: (1428)..(1517)
<223> OTHER INFORMATION: Intron 2.
<220> FEATURE:
<221> NAME/KEY: exon
<222> LOCATION: (1518)..(1583)
<223> OTHER INFORMATION: Exon 3.
<220> FEATURE:

```
<221> NAME/KEY: Intron
<222> LOCATION: (1584)..(1661)
<223> OTHER INFORMATION: Intron 3.
<220> FEATURE:
<221> NAME/KEY: exon
<222> LOCATION: (1662)..(1727)
<223> OTHER INFORMATION: Exon 4.
<220> FEATURE:
<221> NAME/KEY: Intron
<222> LOCATION: (1728)..(1821)
<223> OTHER INFORMATION: Intron 4.
<220> FEATURE:
<221> NAME/KEY: exon
<222> LOCATION: (1822)..(2013)
<223> OTHER INFORMATION: Exon 5 through the stop codon.  Exon 5
      continues beyond this.

<400> SEQUENCE: 3
```

| | |
|---|---:|
| aattacaaaa tatttagaca ataattcata aacatatcat aaataagatc acattcataa | 60 |
| aataaatgag tttttttaga ggacggggttg gcgggacggg tttggcagga cgttacttaa | 120 |
| taacaattgt aaactataca ataaaaatat tttatagata gatacaattt acaaactttt | 180 |
| atatatatta atttaaaaaa taaattgttt tcgcggtata ccgcgggtta aaatctagtt | 240 |
| attcttatt ttgctatgaa ccataattat tttaattact atattatata tatttcccctt | 300 |
| tggatgcatt aaaaaaaggc taatgatcaa ggacatgtta tcgtctttgt attgaccatt | 360 |
| ataatatctg aattttattt tgtgttaaat aatctctcga ataaataatc tttcgaaatg | 420 |
| catgcagttt tattcacact ttatctgtgg acaacaacaa caacaaaaaa gaaggaaaaa | 480 |
| atagattttt gtaatttgtc aaaaatggtg aaactgttgc gagaccttac ttttcaagta | 540 |
| attgtccatt ttcatgttta gtcataataa taattaaata gtctatcaat gctctatctt | 600 |
| atcaatactc ttattttttc aaccgtttca tttactgatt ttcataattt catcccctcc | 660 |
| tctcaattta acttatcaca ttgaaaaaaa caataaaaat gtatgttttt tatttacttg | 720 |
| gtggtccaaa aatgcttttt tcctttttt tattaggtaa aaaatataat attattaaat | 780 |
| aaaattgcta caaaggaaa ctgttcacac acagagtgat gtgagacacc agattctgtc | 840 |
| tatagggatt cgacacgcca ctcgcctctt ttagaacctc cacgcgcttc tctgaagaac | 900 |
| gtgatctcac gcgtcctacc tcccccgcct ataagctta ctacgaaaaa gccacagtga | 960 |
| taatttttac acacagagta gagcagagag agagagagag agagag atg ggt gat | 1015 |
|                                                        Met Gly Asp |  |
|                                                         1          |  |
| tct gac gtc ggt gat cgt ctt ccc cct cca tct tct tcc gac gaa ctc | 1063 |
| Ser Asp Val Gly Asp Arg Leu Pro Pro Pro Ser Ser Ser Asp Glu Leu |  |
|  5              10                  15                           |  |
| tcg agc ttt ctc cga cag att ctt tcc cgt act cct aca gct caa cct | 1111 |
| Ser Ser Phe Leu Arg Gln Ile Leu Ser Arg Thr Pro Thr Ala Gln Pro |  |
| 20               25                  30                  35      |  |
| tct tca cca ccg aag agt act aat gtt tcc tcc gct gag acc ttc ttc | 1159 |
| Ser Ser Pro Pro Lys Ser Thr Asn Val Ser Ser Ala Glu Thr Phe Phe |  |
|                   40                  45                  50     |  |
| cct tcc gtt tcc ggc gga gct gtt tct tcc gtc ggt tat gga gtc tct | 1207 |
| Pro Ser Val Ser Gly Gly Ala Val Ser Ser Val Gly Tyr Gly Val Ser |  |
|             55                  60                  65           |  |
| gaa act ggc caa gac aaa tat gct ttc gaa cac aag gtataaactt | 1253 |
| Glu Thr Gly Gln Asp Lys Tyr Ala Phe Glu His Lys |  |
|       70                  75                   |  |
| aactattctt agctgcagag atgcttcact tggctttcct tgtaaaagaa aacaaaaacc | 1313 |
| aaaattagtc tctttttcttt ttggaatggc taaaacactaa ag aga agt gga gct | 1367 |
|                                                  Arg Ser Gly Ala |  |

|  |  |
|---|---|
| aaa cag aga aat tcg ttg aag aga aac att gat gct caa ttc cac aac<br>Lys Gln Arg Asn Ser Leu Lys Arg Asn Ile Asp Ala Gln Phe His Asn<br>85              90              95 | 1415 |
| ttg tct gaa aag gttttctctt ttatcttcct tttaagattc ttaatttaga<br>Leu Ser Glu Lys<br>100 | 1467 |
| aagaagaaga accttgagat tgtagttgat tagaatctga gtgttagcag aag agg<br>                                                                             Lys Arg<br>                                                                              105 | 1523 |
| agg agc aag atc aac gag aaa atg aaa gct ttg cag aaa ctc att ccc<br>Arg Ser Lys Ile Asn Glu Lys Met Lys Ala Leu Gln Lys Leu Ile Pro<br>              110              115              120 | 1571 |
| aat tcc aac aag gttaatcaat ctttgttcga atcagagata gtgagaaaca<br>Asn Ser Asn Lys<br>              125 | 1623 |
| ttgttctgat tgatccgtta tcttttgttt gtttatag act gat aaa gcc tca atg<br>                                                       Thr Asp Lys Ala Ser Met<br>                                                                                  130 | 1679 |
| ctt gat gaa gct ata gaa tat ctg aag cag ctt caa ctt caa gtc cag<br>Leu Asp Glu Ala Ile Glu Tyr Leu Lys Gln Leu Gln Leu Gln Val Gln<br>              135              140              145 | 1727 |
| gttttttttcc tacttactat gattatatac gttcaaagtc tgatttgtaa attacatcac | 1787 |
| tcagatcatt aacttgattt actgcatgat gcag act tta gcc gtt atg aat ggt<br>                                                       Thr Leu Ala Val Met Asn Gly<br>                                                                        150 | 1842 |
| tta ggc tta aac cct atg cga tta cca cag gtt cca cct cca act cat<br>Leu Gly Leu Asn Pro Met Arg Leu Pro Gln Val Pro Pro Pro Thr His<br>155                  160              165              170 | 1890 |
| aca agg atc aat gag acc tta gag caa gac ctg aac cta gag act ctt<br>Thr Arg Ile Asn Glu Thr Leu Glu Gln Asp Leu Asn Leu Glu Thr Leu<br>              175              180              185 | 1938 |
| ctc gct gct cct cac tcg ctg gaa cca gct aaa aca agt caa gga atg<br>Leu Ala Ala Pro His Ser Leu Glu Pro Ala Lys Thr Ser Gln Gly Met<br>              190              195              200 | 1986 |
| tgc ttt tcc aca gcc act ctg ctt tga agataacatt cagacaatga<br>Cys Phe Ser Thr Ala Thr Leu Leu<br>          205              210 | 2033 |
| tgatgatcgg aattcctcta gtacctgcca gacaggagtg aacaatgttt tgagttttag | 2093 |
| cattggccag atttctatgt tcagttatag ttatgctaat aagctttagg agtgaacaaa | 2153 |
| atctgagtag tttgattata atgatgtctg aagcagatta tatataaaag actaatttac | 2213 |
| ttacatatga gatgattatt acaactatca aatgactatg tctgtgagtt gcatccatcc | 2273 |
| ataagcacac cggtctctac tacttcgagt gattgctgct gctgacttaa ccgcaggtct | 2333 |
| tatcttcgtc attgctttct ctacttgaat tctcacgcca acatccatct gttatttcaa | 2393 |
| atggtaccga taactttagg gatatagaca agacaaattg atattaataa tataacaagg | 2453 |
| ttgtaaagta gaaaccttt ctaaagagca ttgtgtgtct aagatgtggc agaagtatga | 2513 |
| cagttgcttg tacaagtctg cttcagtgta ctgtaaagtc aagagttagt ctgtgaagca | 2573 |
| atagagagat aggagttata aggttgatga tggtatatac cttttcgtaag agggttccgt | 2633 |
| tacagtt | 2640 |

<210> SEQ ID NO 4
<211> LENGTH: 623
<212> TYPE: PRT
<213> ORGANISM: Arabidopsis thaliana

<400> SEQUENCE: 4

```
Met Thr Asp Tyr Arg Leu Gln Pro Thr Met Asn Leu Trp Thr Thr Asp
1               5                   10                  15

Asp Asn Ala Ser Met Met Glu Ala Phe Met Ser Ser Asp Ile Ser
            20                  25                  30

Thr Leu Trp Pro Pro Ala Ser Thr Thr Thr Thr Ala Thr Thr Glu
            35                  40                  45

Thr Thr Pro Thr Pro Ala Met Glu Ile Pro Ala Gln Ala Gly Phe Asn
        50                  55                  60

Gln Glu Thr Leu Gln Gln Arg Leu Gln Ala Leu Ile Glu Gly Thr His
65                  70                  75                  80

Glu Gly Trp Thr Tyr Ala Ile Phe Trp Gln Pro Ser Tyr Asp Phe Ser
                85                  90                  95

Gly Ala Ser Val Leu Gly Trp Gly Asp Gly Tyr Tyr Lys Gly Glu Glu
                100                 105                 110

Asp Lys Ala Asn Pro Arg Arg Ser Ser Ser Pro Pro Phe Ser Thr
            115                 120                 125

Pro Ala Asp Gln Glu Tyr Arg Lys Lys Val Leu Arg Glu Leu Asn Ser
130                 135                 140

Leu Ile Ser Gly Gly Val Ala Pro Ser Asp Asp Ala Val Asp Glu Glu
145                 150                 155                 160

Val Thr Asp Thr Glu Trp Phe Phe Leu Val Ser Met Thr Gln Ser Phe
                165                 170                 175

Ala Cys Gly Ala Gly Leu Ala Gly Lys Ala Phe Ala Thr Gly Asn Ala
            180                 185                 190

Val Trp Val Ser Gly Ser Asp Gln Leu Ser Gly Ser Gly Cys Glu Arg
            195                 200                 205

Ala Lys Gln Gly Gly Val Phe Gly Met His Thr Ile Ala Cys Ile Pro
210                 215                 220

Ser Ala Asn Gly Val Val Glu Val Gly Ser Thr Glu Pro Ile Arg Gln
225                 230                 235                 240

Ser Ser Asp Leu Ile Asn Lys Val Arg Ile Leu Phe Asn Phe Asp Gly
                245                 250                 255

Gly Asp Gly Asp Leu Ser Gly Leu Asn Trp Asn Leu Asp Pro Asp Gln
            260                 265                 270

Gly Glu Asn Asp Pro Ser Met Trp Ile Asn Asp Pro Ile Gly Thr Pro
            275                 280                 285

Gly Ser Asn Glu Pro Gly Asn Gly Ala Pro Ser Ser Ser Ser Gln Leu
            290                 295                 300

Phe Ser Lys Ser Ile Gln Phe Glu Asn Gly Ser Ser Ser Thr Ile Thr
305                 310                 315                 320

Glu Asn Pro Asn Leu Asp Pro Thr Pro Ser Pro Val His Ser Gln Thr
                325                 330                 335

Gln Asn Pro Lys Phe Asn Asn Thr Phe Ser Arg Glu Leu Asn Phe Ser
            340                 345                 350

Asp Val Lys Phe Tyr Phe Ser Glu Pro Arg Ser Gly Glu Ile Leu Asn
            355                 360                 365

Phe Gly Asp Glu Gly Lys Arg Ser Ser Gly Asn Pro Asp Pro Ser Ser
370                 375                 380

Tyr Ser Gly Gln Thr Gln Phe Glu Asn Lys Arg Lys Arg Ser Met Val
385                 390                 395                 400

Leu Asn Glu Asp Lys Val Leu Ser Phe Gly Asp Lys Thr Ala Gly Glu
```

```
                    405                 410                 415
Ser Asp His Ser Asp Leu Glu Ala Ser Val Val Lys Glu Val Ala Val
                420                 425                 430

Glu Lys Arg Pro Lys Arg Gly Arg Lys Pro Ala Asn Gly Arg Glu
            435                 440                 445

Glu Pro Leu Asn His Val Glu Ala Glu Arg Gln Arg Glu Lys Leu
        450                 455                 460

Asn Gln Arg Phe Tyr Ala Leu Arg Ala Val Val Pro Asn Val Ser Lys
465                 470                 475                 480

Met Asp Lys Ala Ser Leu Leu Gly Asp Ala Ile Ala Tyr Ile Asn Glu
                485                 490                 495

Leu Lys Ser Lys Val Val Lys Thr Glu Ser Glu Lys Leu Gln Ile Lys
                500                 505                 510

Asn Gln Leu Glu Glu Val Lys Leu Glu Leu Ala Gly Arg Lys Ala Ser
            515                 520                 525

Pro Ser Gly Gly Asp Met Ser Ser Cys Ser Ser Ile Lys Pro Val
        530                 535                 540

Gly Met Glu Ile Glu Val Lys Ile Ile Gly Trp Asp Ala Met Ile Arg
545                 550                 555                 560

Val Glu Ser Ser Lys Arg Asn His Pro Ala Ala Arg Leu Met Ser Ala
                565                 570                 575

Leu Met Asp Leu Glu Leu Glu Val Asn His Ala Ser Met Ser Val Val
                580                 585                 590

Asn Asp Leu Met Ile Gln Gln Ala Thr Val Lys Met Gly Phe Arg Ile
            595                 600                 605

Tyr Thr Gln Asp Gln Leu Arg Ala Ser Leu Ile Ser Lys Ile Gly
    610                 615                 620

<210> SEQ ID NO 5
<211> LENGTH: 642
<212> TYPE: PRT
<213> ORGANISM: Phaseolus vulgaris

<400> SEQUENCE: 5

Met Thr Glu Tyr Arg Ser Pro Pro Thr Met Asn Leu Trp Thr Asp Asp
1               5                   10                  15

Asn Ala Ser Val Met Glu Ala Phe Met Ser Ser Asp Phe Ser Ser
            20                  25                  30

Leu Trp Leu Pro Thr Pro Gln Ser Ala Ala Ser Thr Thr Thr Pro Gly
        35                  40                  45

Ala Asp Thr Ala Arg Ala Leu Pro Pro Pro Pro Ser Gln Ser Gln
    50                  55                  60

Ser Leu Phe Asn Gln Glu Thr Leu Gln Gln Arg Leu Gln Thr Leu Ile
65                  70                  75                  80

Glu Gly Ala Glu Glu Ser Trp Thr Tyr Ala Ile Phe Trp Gln Ser Ser
                85                  90                  95

Tyr Asp Tyr Ser Ser Ser Thr Ser Leu Leu Gly Trp Gly Asp Gly Tyr
            100                 105                 110

Tyr Lys Gly Glu Glu Asp Lys Gly Lys Gly Lys Ala Pro Lys Glu Met
        115                 120                 125

Ser Ser Ala Glu Gln Asp His Arg Lys Lys Val Leu Arg Glu Leu Asn
    130                 135                 140

Ser Leu Ile Ser Gly Pro Phe Arg Ser Ala Asp Asp Val Asp Glu Glu
145                 150                 155                 160
```

-continued

```
Val Ser Asp Thr Glu Trp Phe Phe Leu Val Ser Met Thr Gln Ser Phe
            165                 170                 175

Leu Ser Gly Ser Gly Leu Pro Gly Gln Ala Phe Leu Asn Ser Ser Pro
            180                 185                 190

Val Trp Val Ala Gly Ala Asp Arg Leu Ser Asp Ser Thr Ser Glu Arg
            195                 200                 205

Ala Arg Gln Gly Gln Val Phe Gly Val Gln Thr Leu Val Cys Ile Pro
210                 215                 220

Ser Ala Asn Gly Val Val Glu Leu Ala Ser Thr Glu Val Ile Phe Gln
225                 230                 235                 240

Asn Ser Asp Leu Met Lys Lys Val Arg Asp Leu Phe Asn Phe Asn Asn
            245                 250                 255

Pro Asp Ala Gly Phe Trp Pro Leu Asn Gln Gly Glu Asn Asp Pro Ser
            260                 265                 270

Ser Leu Trp Leu Asn Pro Ser Ser Ile Glu Ile Lys Asp Thr Ser
            275                 280                 285

Asn Ala Val Ala Leu Val Ser Ala Asn Ala Ser Leu Ser Lys Thr Met
            290                 295                 300

Pro Phe Glu Thr Pro Gly Ser Ser Thr Leu Thr Glu Thr Pro Ser Ala
305                 310                 315                 320

Ala Ala Ala Ala His Val Pro Asn Pro Lys Asn Gln Gly Phe Phe Pro
                    325                 330                 335

Arg Glu Leu Asn Phe Ser Asn Ser Leu Lys Pro Glu Ser Gly Glu Ile
            340                 345                 350

Leu Ser Phe Gly Glu Ser Lys Lys Ser Ser Tyr Asn Gly Ser Tyr Phe
            355                 360                 365

Pro Gly Val Ala Ala Glu Glu Thr Asn Lys Lys Arg Arg Ser Pro Ala
            370                 375                 380

Ser Arg Ser Ser Ile Asp Asp Gly Met Leu Ser Phe Thr Ser Gly Val
385                 390                 395                 400

Ile Ile Pro Ala Ser Asn Ile Lys Ser Gly Ala Val Ala Gly Gly Gly
                    405                 410                 415

Ala Ser Gly Gly Asp Ser Glu Asn Ser Asp Leu Glu Ala Ser Val Val
            420                 425                 430

Lys Glu Ala Asp Ser Arg Val Val Glu Pro Glu Lys Arg Pro Arg Lys
            435                 440                 445

Arg Gly Arg Lys Pro Gly Asn Gly Arg Glu Glu Pro Leu Asn His Val
            450                 455                 460

Glu Ala Glu Arg Gln Arg Arg Glu Lys Leu Asn Gln Arg Phe Tyr Ala
465                 470                 475                 480

Leu Arg Ala Val Val Pro Asn Val Ser Lys Met Asp Lys Ala Ser Leu
                    485                 490                 495

Leu Gly Asp Ala Ile Ser Tyr Ile Asn Glu Leu Lys Ser Lys Leu Ser
            500                 505                 510

Glu Leu Glu Ser Glu Lys Gly Glu Leu Glu Lys Gln Leu Glu Leu Val
            515                 520                 525

Lys Lys Glu Leu Glu Leu Ala Thr Lys Ser Pro Ser Pro Pro Pro Gly
530                 535                 540

Pro Pro Pro Ser Asn Lys Glu Ala Lys Glu Thr Thr Ser Lys Leu Ile
545                 550                 555                 560

Asp Leu Glu Leu Glu Val Lys Ile Ile Gly Trp Asp Ala Met Ile Arg
                    565                 570                 575

Ile Gln Cys Ser Lys Lys Asn His Pro Ala Ala Arg Leu Met Ala Ala
```

```
                      580              585             590
Leu Lys Glu Leu Asp Leu Asp Val Asn His Ala Ser Val Ser Val Val
        595                 600                 605

Asn Asp Leu Met Ile Gln Gln Ala Thr Val Asn Met Gly Asn Arg Phe
    610                 615                 620

Tyr Thr Gln Glu Gln Leu Arg Ser Ala Arg Ser Ser Lys Ile Gly Asn
625                 630                 635                 640

Ala Leu

<210> SEQ ID NO 6
<211> LENGTH: 610
<212> TYPE: PRT
<213> ORGANISM: Zea mays

<400> SEQUENCE: 6

Met Ala Leu Ser Ala Ser Arg Val Gln Gln Ala Glu Glu Leu Leu Gln
1               5                   10                  15

Arg Pro Ala Glu Arg Gln Leu Met Arg Ser Gln Leu Ala Ala Ala Ala
            20                  25                  30

Arg Ser Ile Asn Trp Ser Tyr Ala Leu Phe Trp Ser Ile Ser Asp Thr
        35                  40                  45

Gln Pro Gly Val Leu Thr Trp Thr Asp Gly Phe Tyr Asn Gly Glu Val
    50                  55                  60

Lys Thr Arg Lys Ile Ser Asn Ser Val Glu Leu Thr Ser Asp Gln Leu
65                  70                  75                  80

Val Met Gln Arg Ser Asp Gln Leu Arg Glu Leu Tyr Glu Ala Leu Leu
                85                  90                  95

Ser Gly Glu Gly Asp Arg Arg Ala Ala Pro Ala Arg Pro Ala Gly Ser
            100                 105                 110

Leu Ser Pro Glu Asp Leu Gly Asp Thr Glu Trp Tyr Tyr Val Val Ser
        115                 120                 125

Met Thr Tyr Ala Phe Arg Pro Gly Gln Gly Leu Pro Gly Arg Ser Phe
    130                 135                 140

Ala Ser Asp Glu His Val Trp Leu Cys Asn Ala His Leu Ala Gly Ser
145                 150                 155                 160

Lys Ala Phe Pro Arg Ala Leu Leu Ala Lys Ser Ala Ser Ile Gln Ser
                165                 170                 175

Ile Leu Cys Ile Pro Val Met Gly Gly Val Leu Glu Leu Gly Thr Thr
            180                 185                 190

Asp Thr Val Pro Glu Ala Pro Asp Leu Val Ser Arg Ala Thr Ala Ala
        195                 200                 205

Phe Trp Glu Pro Gln Cys Pro Ser Ser Pro Ser Gly Arg Ala Asn
    210                 215                 220

Glu Thr Gly Glu Ala Ala Asp Asp Gly Thr Phe Ala Phe Glu Glu
225                 230                 235                 240

Leu Asp His Asn Asn Gly Met Asp Ile Glu Ala Met Thr Ala Ala
                245                 250                 255

Gly Gly His Gly Gln Glu Glu Leu Arg Leu Arg Glu Glu Ala
            260                 265                 270

Leu Ser Asp Asp Ala Ser Leu Glu His Ile Thr Lys Glu Ile Glu Glu
        275                 280                 285

Phe Tyr Ser Leu Cys Asp Glu Met Asp Leu Gln Ala Leu Pro Leu Pro
    290                 295                 300

Leu Glu Asp Gly Trp Thr Val Asp Ala Ser Asn Phe Glu Val Pro Cys
```

```
                305                 310                 315                 320

Ser Ser Pro Gln Pro Ala Pro Pro Val Asp Arg Ala Thr Ala Asn
                    325                 330                 335

Val Ala Ala Asp Ala Ser Arg Ala Pro Val Tyr Gly Ser Arg Ala Thr
                340                 345                 350

Ser Phe Met Ala Trp Thr Arg Ser Ser Gln Gln Ser Ser Cys Ser Asp
                355                 360                 365

Asp Ala Ala Pro Ala Ala Val Val Pro Ala Ile Glu Glu Pro Gln Arg
            370                 375                 380

Leu Leu Lys Lys Val Val Ala Gly Gly Ala Trp Glu Ser Cys Gly
385                 390                 395                 400

Gly Ala Thr Gly Ala Ala Gln Glu Met Ser Gly Thr Gly Thr Lys Asn
                    405                 410                 415

His Val Met Ser Glu Arg Lys Arg Arg Glu Lys Leu Asn Glu Met Phe
                420                 425                 430

Leu Val Leu Lys Ser Leu Leu Pro Ser Ile His Arg Val Asn Lys Ala
                435                 440                 445

Ser Ile Leu Ala Glu Thr Ile Ala Tyr Leu Lys Glu Leu Gln Arg Arg
450                 455                 460

Val Gln Glu Leu Glu Ser Ser Arg Glu Pro Ala Ser Arg Pro Ser Glu
465                 470                 475                 480

Thr Thr Thr Arg Leu Ile Thr Arg Pro Ser Arg Gly Asn Asn Glu Ser
                485                 490                 495

Val Arg Lys Glu Val Cys Ala Gly Ser Lys Arg Lys Ser Pro Glu Leu
                500                 505                 510

Gly Arg Asp Asp Val Glu Arg Pro Pro Val Leu Thr Met Asp Ala Gly
                515                 520                 525

Thr Ser Asn Val Thr Val Thr Val Ser Asp Lys Asp Val Leu Leu Glu
        530                 535                 540

Val Gln Cys Arg Trp Glu Glu Leu Leu Met Thr Arg Val Phe Asp Ala
545                 550                 555                 560

Ile Lys Ser Leu His Leu Asp Val Leu Ser Val Gln Ala Ser Ala Pro
                565                 570                 575

Asp Gly Phe Met Gly Leu Lys Ile Arg Ala Gln Phe Ala Gly Ser Gly
                580                 585                 590

Ala Val Val Pro Trp Met Ile Ser Glu Ala Leu Arg Lys Ala Ile Gly
            595                 600                 605

Lys Arg
    610

<210> SEQ ID NO 7
<211> LENGTH: 562
<212> TYPE: PRT
<213> ORGANISM: Zea mays

<400> SEQUENCE: 7

Met Ala Leu Ser Ala Ser Pro Ala Gln Glu Glu Leu Leu Gln Pro Ala
1               5                   10                  15

Gly Arg Pro Leu Arg Lys Gln Leu Ala Ala Ala Arg Ser Ile Asn
            20                  25                  30

Trp Ser Tyr Ala Leu Phe Trp Ser Ile Ser Ser Thr Gln Arg Pro Arg
                35                  40                  45

Val Leu Thr Trp Thr Asp Gly Phe Tyr Asn Gly Glu Val Lys Thr Arg
        50                  55                  60
```

-continued

```
Lys Ile Ser His Ser Val Glu Leu Thr Ala Asp Gln Leu Leu Met Gln
 65                  70                  75                  80

Arg Ser Glu Gln Leu Arg Glu Leu Tyr Glu Ala Leu Arg Ser Gly Glu
                 85                  90                  95

Cys Asp Arg Arg Gly Ala Arg Pro Val Gly Ser Leu Ser Pro Glu Asp
            100                 105                 110

Leu Gly Asp Thr Glu Trp Tyr Tyr Val Ile Cys Met Thr Tyr Ala Phe
        115                 120                 125

Leu Pro Gly Gln Gly Leu Pro Gly Arg Ser Ser Ala Ser Asn Glu His
    130                 135                 140

Val Trp Leu Cys Asn Ala His Leu Ala Gly Ser Lys Asp Phe Pro Arg
145                 150                 155                 160

Ala Leu Leu Ala Lys Ser Ala Ser Ile Gln Thr Ile Val Cys Ile Pro
                165                 170                 175

Leu Met Gly Gly Val Leu Glu Leu Gly Thr Thr Asp Lys Val Pro Glu
            180                 185                 190

Asp Pro Asp Leu Val Ser Arg Ala Thr Val Ala Phe Trp Glu Pro Gln
        195                 200                 205

Cys Pro Thr Tyr Ser Lys Glu Pro Ser Ser Asn Pro Ser Ala Tyr Glu
    210                 215                 220

Thr Gly Glu Ala Ala Tyr Ile Val Leu Glu Asp Leu Asp His Asn
225                 230                 235                 240

Ala Met Asp Met Glu Thr Val Thr Ala Ala Gly Arg His Gly Thr
                245                 250                 255

Gly Gln Glu Leu Gly Glu Val Glu Ser Pro Ser Asn Ala Ser Leu Glu
            260                 265                 270

His Ile Thr Lys Gly Ile Asp Glu Phe Tyr Ser Leu Cys Glu Glu Met
        275                 280                 285

Asp Val Gln Pro Leu Glu Asp Ala Trp Ile Met Asp Gly Ser Asn Phe
    290                 295                 300

Glu Val Pro Ser Ser Ala Leu Pro Val Asp Gly Ser Ser Ala Pro Ala
305                 310                 315                 320

Asp Gly Ser Arg Ala Thr Ser Phe Val Val Trp Thr Arg Ser Ser His
                325                 330                 335

Ser Cys Ser Gly Glu Ala Ala Val Pro Val Ile Glu Glu Pro Gln Lys
            340                 345                 350

Leu Leu Lys Lys Ala Leu Ala Gly Gly Gly Ala Trp Ala Asn Thr Asn
        355                 360                 365

Cys Gly Gly Gly Gly Thr Thr Val Thr Ala Gln Glu Asn Gly Ala Lys
    370                 375                 380

Asn His Val Met Ser Glu Arg Lys Arg Glu Lys Leu Asn Glu Met
385                 390                 395                 400

Phe Leu Val Leu Lys Ser Leu Val Pro Ser Ile His Lys Val Asp Lys
                405                 410                 415

Ala Ser Ile Leu Ala Glu Thr Ile Ala Tyr Leu Lys Glu Leu Gln Arg
            420                 425                 430

Arg Val Gln Glu Leu Glu Ser Arg Arg Gln Gly Gly Ser Gly Cys Val
        435                 440                 445

Ser Lys Lys Val Cys Val Gly Ser Asn Ser Lys Arg Lys Ser Pro Glu
    450                 455                 460

Phe Ala Gly Gly Ala Lys Glu His Pro Trp Val Leu Pro Met Asp Gly
465                 470                 475                 480

Thr Ser Asn Val Thr Val Thr Val Ser Asp Thr Asn Val Leu Leu Glu
```

```
                485              490              495
Val Gln Cys Arg Trp Glu Lys Leu Leu Met Thr Arg Val Phe Asp Ala
        500              505              510
Ile Lys Ser Leu His Leu Asp Ala Leu Ser Val Gln Ala Ser Ala Pro
        515              520              525
Asp Gly Phe Met Arg Leu Lys Ile Gly Ala Gln Phe Ala Gly Ser Gly
        530              535              540
Ala Val Val Pro Gly Met Ile Ser Gln Ser Leu Arg Lys Ala Ile Gly
545              550              555              560
Lys Arg

<210> SEQ ID NO 8
<211> LENGTH: 22
<212> TYPE: DNA
<213> ORGANISM: Arabidopsis thaliana

<400> SEQUENCE: 8
gaagaggagg agcaagatca ac                                              22

<210> SEQ ID NO 9
<211> LENGTH: 14
<212> TYPE: DNA
<213> ORGANISM: Arabidopsis thaliana

<400> SEQUENCE: 9
gaagaggagg acct                                                       14

<210> SEQ ID NO 10
<211> LENGTH: 17
<212> TYPE: DNA
<213> ORGANISM: Arabidopsis thaliana

<400> SEQUENCE: 10
agaggagcaa gatcaac                                                    17

<210> SEQ ID NO 11
<211> LENGTH: 31
<212> TYPE: DNA
<213> ORGANISM: Arabidopsis thaliana

<400> SEQUENCE: 11
gaagaggagg accttaagga gcaagatcaa c                                    31

<210> SEQ ID NO 12
<211> LENGTH: 32
<212> TYPE: DNA
<213> ORGANISM: Arabidopsis thaliana

<400> SEQUENCE: 12
gaggaggagg acctctgagg agcaagatca ac                                   32

<210> SEQ ID NO 13
<211> LENGTH: 51
<212> TYPE: DNA
<213> ORGANISM: Arabidopsis thaliana

<400> SEQUENCE: 13
aagagaaaca ttgatgctca attccacaac ttgtctgaaa agaagaggag g              51

<210> SEQ ID NO 14
<211> LENGTH: 24
```

<212> TYPE: DNA
<213> ORGANISM: Arabidopsis thaliana

<400> SEQUENCE: 14
gaagaggaag acgatgaaga ggat                                            24

<210> SEQ ID NO 15
<211> LENGTH: 904
<212> TYPE: DNA
<213> ORGANISM: Arabidopsis thaliana
<220> FEATURE:
<221> NAME/KEY: CDS
<222> LOCATION: (23)..(625)

<400> SEQUENCE: 15

```
agagagagag agagagagag ag atg ggt gat tct gac gtc ggt gat cgt ctt        52
                         Met Gly Asp Ser Asp Val Gly Asp Arg Leu
                          1               5                  10 ccc cct cca tct tct tcc gac gaa ctc tcg agc ttt ctc cga cag att        100
Pro Pro Pro Ser Ser Ser Asp Glu Leu Ser Ser Phe Leu Arg Gln Ile
             15                  20                  25 ctt tcc cgt act cct aca gct caa cct tct tca cca ccg aag agt act        148
Leu Ser Arg Thr Pro Thr Ala Gln Pro Ser Ser Pro Pro Lys Ser Thr
         30                  35                  40 aat gtt tcc tcc gct gag acc ttc ttc cct tcc gtt tcc ggc gga gct        196
Asn Val Ser Ser Ala Glu Thr Phe Phe Pro Ser Val Ser Gly Gly Ala
     45                  50                  55 gtt tct tcc gtc ggt tat gga gtc tct gaa act ggc caa gac aaa tat        244
Val Ser Ser Val Gly Tyr Gly Val Ser Glu Thr Gly Gln Asp Lys Tyr
 60                  65                  70 gct ttc gaa cac aag aga agt gga gct aaa cag aga aat tcg ttg gaa        292
Ala Phe Glu His Lys Arg Ser Gly Ala Lys Gln Arg Asn Ser Leu Glu
 75                  80                  85                  90 gag gaa gac gat gaa gag gat agc aag atc aac gag aaa atg aaa gct        340
Glu Glu Asp Asp Glu Glu Asp Ser Lys Ile Asn Glu Lys Met Lys Ala
                 95                 100                 105 ttg cag aaa ctc att ccc aat tcc aac aag act gat aaa gcc tca atg        388
Leu Gln Lys Leu Ile Pro Asn Ser Asn Lys Thr Asp Lys Ala Ser Met
             110                 115                 120 ctt gat gaa gct ata gaa tat ctg aag cag ctt caa ctt caa gtc cag        436
Leu Asp Glu Ala Ile Glu Tyr Leu Lys Gln Leu Gln Leu Gln Val Gln
         125                 130                 135 act tta gcc gtt atg aat ggt tta ggc tta aac cct atg cga tta cca        484
Thr Leu Ala Val Met Asn Gly Leu Gly Leu Asn Pro Met Arg Leu Pro
     140                 145                 150 cag gtt cca cct cca act cat aca agg atc aat gag acc tta gag caa        532
Gln Val Pro Pro Pro Thr His Thr Arg Ile Asn Glu Thr Leu Glu Gln
155                 160                 165                 170 gac ctg aac cta gag act ctt ctc gct gct cct cac tcg ctg gaa cca        580
Asp Leu Asn Leu Glu Thr Leu Leu Ala Ala Pro His Ser Leu Glu Pro
                 175                 180                 185 gct aaa aca agt caa gga atg tgc ttt tcc aca gcc act ctg ctt            625
Ala Lys Thr Ser Gln Gly Met Cys Phe Ser Thr Ala Thr Leu Leu
             190                 195                 200 tgaagataac attcagacaa tgatgatgat cggaattcct ctagtacctg ccagacagga      685
gtgaacaatg ttttgagttt tagcattggc cagatttcta tgttcagtta tagttatgct      745
aataagcttt aggagtgaac aaaatctgag tagtttgatt ataatgatgt ctgaagcaga      805
ttatatataa aagactaatt tacttacata tgagatgatt attacaacta tcaaatgact      865
atgtctgtga gttgcatcca aaaaaaaaaa aaaaaaaa                              904
```

```
<210> SEQ ID NO 16
<211> LENGTH: 201
<212> TYPE: PRT
<213> ORGANISM: Arabidopsis thaliana

<400> SEQUENCE: 16

Met Gly Asp Ser Asp Val Gly Asp Arg Leu Pro Pro Ser Ser Ser
1               5                  10                  15

Asp Glu Leu Ser Ser Phe Leu Arg Gln Ile Leu Ser Arg Thr Pro Thr
                20                  25                  30

Ala Gln Pro Ser Ser Pro Pro Lys Ser Thr Asn Val Ser Ser Ala Glu
                35                  40                  45

Thr Phe Phe Pro Ser Val Ser Gly Gly Ala Val Ser Ser Val Gly Tyr
    50                  55                      60

Gly Val Ser Glu Thr Gly Gln Asp Lys Tyr Ala Phe Glu His Lys Arg
65                  70                  75                  80

Ser Gly Ala Lys Gln Arg Asn Ser Leu Glu Glu Glu Asp Asp Glu Glu
                85                  90                  95

Asp Ser Lys Ile Asn Glu Lys Met Lys Ala Leu Gln Lys Leu Ile Pro
                100                 105                 110

Asn Ser Asn Lys Thr Asp Lys Ala Ser Met Leu Asp Glu Ala Ile Glu
                115                 120                 125

Tyr Leu Lys Gln Leu Gln Leu Gln Val Gln Thr Leu Ala Val Met Asn
    130                 135                 140

Gly Leu Gly Leu Asn Pro Met Arg Leu Pro Gln Val Pro Pro Thr
145                 150                 155                 160

His Thr Arg Ile Asn Glu Thr Leu Glu Gln Asp Leu Asn Leu Glu Thr
                165                 170                 175

Leu Leu Ala Ala Pro His Ser Leu Glu Pro Ala Lys Thr Ser Gln Gly
                180                 185                 190

Met Cys Phe Ser Thr Ala Thr Leu Leu
                195                 200
```

DEHISCENCE GENE AND METHODS FOR REGULATING DEHISCENCE

This application is a 371 of PCT/SG01/00017 filed Feb. 2, 2001, which claims the benefit of SINGAPORE application number SG00/00022 filed Feb. 11, 2000.

BACKGROUND OF THE INVENTION

The present invention is directed to a mutation in *Arabidopsis thaliana* which prevents dehiscence (pod shattering) of the mature fruit. The isolated gene is identified as SGT10166 and encodes a protein that was found to be similar to the basic Helix-loop-Helix class of transcription factors. The expression pattern of the gene and the phenotype of the mutant plants indicates its role in silique dehiscence.

The publications and other materials used herein to illuminate the background of the invention or provide additional details respecting the practice are respectively grouped in the appended Lists of References.

The fruit is a specialized plant organ which is responsible for the maturation and dispersal of seeds. Dispersal of seeds occurs through a process of dehiscence, e.g., where a seed pod opens to release the seeds therein. Dehiscence is of agronomic importance in crops like *Brassica* sp., where it leads to significant seed loss during harvest.

The fruit of *Arabidopsis* is known as silique, which develops from a fertilized gynoecium. The gynoecium consists of an apical stigma, a style and a basal ovary. The ovary consists of two carpels that share a fused tissue called septum. The walls of the carpel are known as valves, which are joined to the replum. The replum represents the outer margin of the septum (Sessions, 1999). After fertilization, the gynoecium expands to form an elongated silique. Dispersal of seeds occurs through a process of dehiscence where the silique opens to release the seeds. Dehiscence in *Arabidopsis* requires the development of a dehiscence zone along the replum-valve junction which allows the valves to detach from the replum, releasing the seeds (Gu et al., 1998).

Thus, there is a continued need to investigate genes involved in the dispersal of seeds through the process of dehiscence as the prevention of dehiscence in crops would significantly minimize seed loss during harvest.

It is also desired to identify plant genes which are involved with dehiscence in order to derive promoter and/or enhancer and/or intron sequences for use in preparing transgenic plants or in order to interfere with normal dehiscence in transgenic plants to produce indehiscent plants.

SUMMARY OF THE INVENTION

The present invention is directed to a gene which is involved in dehiscence, mutations in the gene which prevent dehiscence and constructs which inhibit the activity of the gene product. The present invention is further directed to the prevention of the dispersal of seeds through the process of dehiscence (pod shattering), which leads to significant seed loss during harvesting of crops. In accordance with the present invention, we have identified a gene in *Arabidopsis thaliana* which is involved in dehiscence and a mutation thereof which prevents dehiscence of the mature fruit (silique). The gene encodes a protein that was found to be similar to the basic Helix-loop-Helix class of transcription factors.

In a one aspect, the present invention is directed to the identification and characterization of the SGT10166 gene in *Arabidopsis thaliana*.

In a second aspect, the present invention is directed to mutations in *Arabidopsis thaliana* and other plants that prevent dehiscence of the mature fruit.

In a third aspect of the invention, constructs comprising at least a portion of an SGT10166 nucleic acid are provided for altering dehiscence of the mature fruit. The constructs generally comprise a heterologous promoter, i.e., one not naturally associated with the SGT10166 gene, operably linked to the SGT10166 nucleic acid. The SGT10166 may be in sense or antisense orientation with respect to the promoter. Vectors containing the construct for use in transforming plant cells are also provided. Any plant cells can be transformed in accordance with the present invention. Preferred plant cells are plant cells of plants which develop fruit, e.g., silique, which develops from a fertilized gynoecium to produce seeds in a pod.

In a fourth aspect of the invention, plants having at least one cell transformed with a construct containing SGT10166 nucleic acid for altering dehiscence of the mature fruit is provided. Such plants have a phenotype characterized by altered debiscence. Preferred plant cells are plant cells of plants which develop fruit, e.g., silique, which develops from a fertilized gynoecium to produce seeds in a pod.

In a fifth aspect of the invention, methods for producing plants having altered dehiscence are provided. The methods comprise the steps of transforming plant cells with a vector comprising at least a portion of an SGT10166 nucleic acid, regenerating plants from one or more of the transformed plant cells and selecting at least one plant exhibiting altered dehiscence.

In a sixth aspect of the invention, a promoter, an enhancer and/or an intron of the *Arabidopsis* SGT10166 gene are provided.

In a seventh aspect of the invention, gene constructs comprising the promoter and/or enhancer and/or intron of the SGT10166 gene and a heterologous gene are provided. Vectors containing these constructs are also provided. Plants having at least one cell containing these constructs are further provided by the invention.

BRIEF DESCRIPTION OF THE FIGURES

FIG. 4(*a*) depicts the cDNA (SEQ ID NO:1) and deduced amino acid sequence (SEQ ID NO:2) of SGT10166. FIG. 4(*b*1–*b*4) depicts a sequence comparison of SGT10166 (SEQ ID NO:2) to some plant myc proteins (SEQ ID NOs:3–6).

FIG. 5 shows the genomic sequence flanking the Ds insertion site and the footprint analysis. (1) Region of wildtype ALC locus prior to DsG insertion (SEQ ID NO:8). (2) Sequence alteration at ALC locus after Ds insertion. Nucleotides in bold represent the bases added during Ds insertion (SEQ ID NOs:9 and 10). (3) and (4) show the 9 base pair and 10 base pair footprint (in bold) observed after Ds excision (SEQ ID NOs:11 and 12).

BRIEF DESCRIPTION OF THE SEQUENCES

Figure 1:
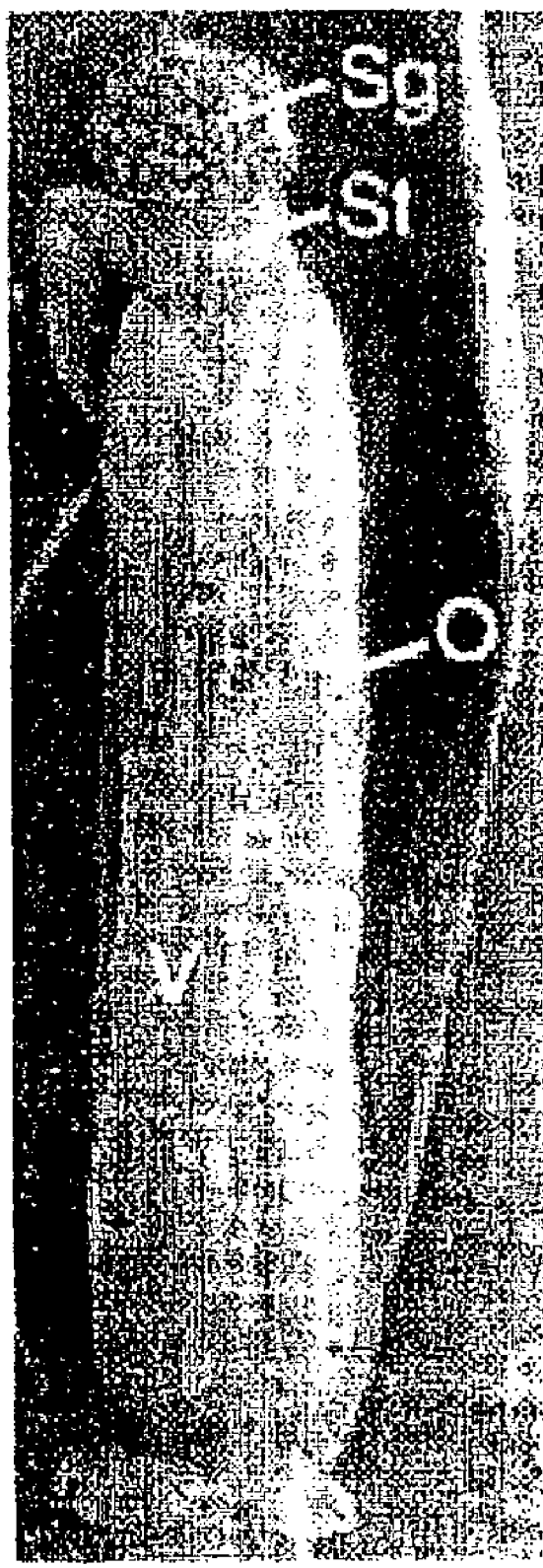
FIG. 1 depicts the structure of wild type gynoecium. Sg—Stigma; St—Style; O—Ovary; R—Replum; V—Valve.

SEQ ID NO:1 is the nucleotide sequence for the cDNA of SGT10166.

SEQ ID NO:2 is amino acid sequence for the SGT10166 polypeptide.

SEQ ID NO:3 is the nucleotide sequence for the genomic DNA of SGT10166.

SEQ ID NO:4 is amino acid sequence for the rd22BP1 polypeptide.

SEQ ID NO:5 amino acid sequence for the PGI polypeptide.

SEQ ID NO:6 amino acid sequence for the Lc polypeptide.

SEQ ID NO:7 amino acid sequence for the B-Peru polypeptide.

SEQ ID NO:8 is a region of wildtype ALC locus prior to DsG insertion.

SEQ ID NO:9 is a region of the ALC locus after Ds insertion.

SEQ ID NO:10 is a region of the ALC locus after Ds insertion.

SEQ ID NO:11 is a region of the ALC locus of a revertant after Ds excision.

SEQ ID NO:12 is a region of the ALC locus (alc 10) after Ds excision.

SEQ ID NO:13 is the DNA fragment deleted from SEQ ID NO:1 and which encodes a basic peptide domain and is replaced by a sequence encoding an acidic domain in SEQ ID NO:14.

SEQ ID NO:15 is the dominant negative DNA construct created by deleting the basic domain encoding portion (SEQ ID NO:13) of SGT10166 and inserting SEQ ID NO:14.

SEQ ID NO:16 is the protein encoded by SEQ ID NO:15.

DETAILED DESCRIPTION OF THE INVENTION

The present invention is directed to a gene involved in dehiscence and to mutations in the gene which prevent dehiscence (pod shattering) of the mature fruit. The SGT10166 gene encodes a protein similar to the basic Helix-loop-Helix class of transcription factors. The expression pattern of the gene and the phenotype of the mutant plants indicates its role in enabling silique dehiscence.

In accordance with the present invention, a gene is provided which is involved in dehiscence. This gene was discovered by identifying an *Arabidopsis* line containing a mutation which prevented dehiscence. More specifically, the isolated gene encodes a protein that was found to be similar to the basic Helix-loop-Helix class of transcription factors. It was found that the protein product was found in the gynoecium as more fully described in Example 2. The cDNA coding for the wild-type gene was discovered on the basis of the mutant gene, as more fully described in Example 3. The *Arabidopsis* gene can be used to screen genomic DNA of plants having seed pods to identify homologous genes, which provide additional nucleic acids for use in inhibiting dehiscence. The gene identified in accordance with the present invention is termed the SGT10166 gene.

The process of dehiscence, commonly known as pod shatter, is of agronomic importance in crops such as oil seed rape (*Brassica napus*) which results in seed loss causing low yields. The losses can be as high as 50% under adverse conditions (Coupe et al., 1994). The mutant line SGT10166 shows an indehiscent phenotype whereby the silique fail to open, and the protein resembles the bHLH family of proteins. Thus, the SGT10166 gene and homologous genes are useful for making plants which have an indehiscent phenotype. The indehiscent phenotype can be accomplished using an anti-sense or a dominant negative approach. For the antisense approach (Gray et al., 1992), it may be necessary to first clone the corresponding gene from the desired crop plant by DNA homology to the SGT10166 gene. Dominant negative regulators can be made by deleting or mutating the DNA binding domain of the protein (Krylov et al., 1997). Such HLH proteins act as dominant negative regulators by sequestering bHLH proteins to form inactive protein dimers. In this approach, the *Arabidopsis* gene may be used directly.

Methods of interfering with gene function in a transgenic plant include introducing a synthetic gene that causes sense or antisense suppression of the target gene (Taylor and Jorgensen, 1992). The suppression methods require substantial similarity between the target gene and the suppressing gene, greater than 80% nucleotide sequence identity (Mol et al., 1994).

As described in further detail herein, the SGT10166 gene can be used to prevent normal dehiscence of the mature fruit in plants. Briefly, two techniques for using the SGT10166 gene for this purpose are antisense or sense suppression to decrease the level of expression of the endogenous SGT10166 gene. A third technique is to use the regulatory sequences of SGT10166 to direct expression of a lethal gene product specifically in fruit tissues (genetic ablation).

Definitions

The present invention employs the following definitions, which are, where appropriate, referenced to SGT10166.

"Altered dehiscence" or "modified dehiscence phenotype" refers to a physical modification in the structure of a plant's silique tissue as compared to the parent plant from which the plant having the modified phenotype is obtained. Macroscopic alterations may include changes in the size, shape, number or location of fruit organs. Microscopic alterations may include changes in the types or shapes of cells that make up the fruit structures. Such modified fruit phenotypes can be uniform throughout the plant and typically arise when each of the cells within the plant contain cells transformed with a vector comprising at least a portion of the SGT10166 nucleic acid. Such plants are sometimes referred to as transgenic plants. The phenotype produced in a particular plant is dependent upon the design of the vector used to produce it. Thus, the vector can be designed to transcribe a nucleic acid which encodes at least a portion of the SGT10166 protein. In such cases, the SGT10166 protein so produced is capable of conferring a particular phenotype based on the presence of that protein within the cell. Alternatively, the vector can be constructed such that transcription results in the formation of a transcript which is capable of hybridizing with an RNA transcript of an endogenous SGT10166 or a homolog gene. This approach employs the well known antisense technology and results in a modulation in the phenotypic effect of the endogenous SGT10166 genes. Such modulation of the endogenous SGT10166 gene can also potentially be obtained by using the sense strand of the SGT10166 gene to cause sense suppression of the endogenous SGT10166 alleles as well as the SGT10166 gene introduced in the vector. The production of a plant containing such a phenotype is contemplated based upon the sense suppression observed in *Petunia hybrida* as set forth in PCT Publication WO 90/12084. The vector may comprise the SGT10166 promoter regulating transcription of a gene encoding a protein that interferes will cell growth. In such cases, the altered dehiscence exhibited may be severe atrophy or loss of fruit structures.

"Amplification of polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al. (1990) (for PCR); Wu and Wallace (1989) (for LCR); U.S. Pat. Nos. 5,270,184 and 5,455,166 and Walker et al. (1992) (for SDA); Spargo et al. (1996) (for thermophilic SDA) and U.S. Pat. No. 5,409,818, Fahy et al. (1991) and Compton (1991) (for 3SR and NASBA). Reagents and hardware for conducting PCR are commercially available. Primers useful to amplify sequences from the SGT10166 region are preferably complementary to, and hybridize specifically to sequences in the SGT10166 region or in regions that flank a target region therein. SGT10166 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al. (1986).

"Analyte polynucleotide" and "analyte strand" refer to a single- or double-stranded polynucleotide which is suspected of containing a target sequence, and which may be present in a variety of types of samples, including biological samples.

"Binding partner" refers to a molecule capable of binding a ligand molecule with high specificity, as for example, complementary polynucleotide strands or an enzyme and its inhibitor. In general, the specific binding partners must bind with sufficient affinity to immobilize the analyte copy/complementary strand duplex (in the case of polynucleotide hybridization) under the isolation conditions. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from a plant including, but not limited to, e.g., pollen, ovules, cells, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the MRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native plant sequence or protein, e.g., ribosomes, polymerase, many other plant genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"SGT10166 allele" refers, respectively, to normal alleles of the SGT10166 locus as well as alleles of SGT10166 having variations, isolated from plants or produced in accordance with the present invention.

"SGT10166 locus", "SGT10166 gene", "SGT10166 nucleic acids" or "SGT10166 polynucleotide" each refer to polynucleotides, all of which are in the SGT10166 region, respectively, that are likely to be expressed in normal tissue and involved in dehiscence. The SGT10166 locus is intended to include coding sequences, intervening sequences and regulatory elements (e.g., promoters and enhancers) controlling transcription and/or translation. The SGT10166 locus is intended to include all allelic variations of the DNA sequence.

These terms, when applied to a nucleic acid, refer to a nucleic acid which encodes a plant SGT10166 polypeptide, fragment, homolog or variant, including, e.g., protein fusions or deletions. The nucleic acids of the present invention will possess a sequence which is either derived from, or substantially similar to, a natural SGT10166-encoding gene or one having substantial homology with a natural SGT10166-encoding gene or a portion thereof. The term SGT10166 nucleic acid is sometimes used to refer to the sense and antisense strands of the SGT10166 gene collectively.

The SGT10166 gene or nucleic acid includes normal alleles of the SGT10166 gene, respectively, including silent alleles having no effect on the amino acid sequence of the SGT10166 polypeptide as well as alleles leading to amino acid sequence variants of the SGT10166 polypeptide that do not substantially affect its function. These terms also include alleles having one or more mutations which adversely affect the function of the SGT10166 polypeptide. A mutation may be a change in the SGT10166 nucleic acid sequence which produces a deleterious change in the amino acid sequence of the SGT10166 polypeptide, resulting in partial or complete loss of SGT10166 function, respectively, or may be a change in the nucleic acid sequence which results in the loss of effective SGT10166 expression or the production of aberrant forms of the SGT10166 polypeptide.

The SGT10166 nucleic acid may be that shown in SEQ ID NO:1 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:1 yet encode a polypeptide with the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The SGT10166 gene, respectively, also refers to (a) any DNA sequence that (i) hybridizes to the complement of the DNA sequences that encode the amino acid sequence set forth in SEQ ID NO:2 under highly stringent conditions (Ausubel et al., 1992) and (ii) encodes a gene product functionally equivalent to SGT10166, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992) and (ii) encodes a gene product functionally equivalent to SGT10166. The invention also includes nucleic acid molecules that are the complements of the sequences described herein.

The polynucleotide compositions of this invention include RNA, CDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the SGT10166 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it may also be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of CDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an SGT10166-encoding sequence. In this context, oligomers of as low as 8 nucleotides, more generally 8–17 nucleotides, can be used for probes, especially in connection with chip technology.

Techniques for nucleic acid manipulation are described generally, e.g., in Sambrook et al. (1989) or Ausubel et al. (1992). Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the SGT10166 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1, its complement or functionally equivalent nucleic acid sequences. The present invention does not include nucleic acids which exist in the prior art. That is, the present invention includes all nucleic acids having at least 8 nucleotides derived from SEQ ID NO:1 with the proviso that it does not include isolated nucleic acids existing in the prior art.

"SGT10166 protein" or "SGT10166 polypeptide" refers to a protein or polypeptide encoded by the SGT10166 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native SGT10166 sequence, preferably in excess of about 90%, and more preferably at least about 95% homologous. Also included are proteins encoded by DNA which hybridize under high or low stringency conditions, to SGT10166-encoding nucleic acids and closely related polypeptides or proteins retrieved by antisera to the SGT10166 protein(s).

The SGT10166 polypeptide may be that shown in SEQ ID NO:2 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the SGT10166 polypeptide. Such polypeptides may have an amino acid sequence which differs from that set forth in SEQ ID NO:2 by one or more of addition, substitution, deletion or insertion of one or more amino acids. In one embodiment, these variant polypeptides have a function similar to SGT10166 such that they can be used to restore fertility or used in place of homologous genes. In a second embodiment, these variant peptides do not retain the SGT10166 function such that they can be used as a dominant negative.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the SGT10166 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression. "Probes". Probes for SGT10166 alleles may be derived from the sequences of the SGT10166 region, its cDNA, functionally equivalent sequences, or the complements thereof. The probes may be of any suitable length, which span all or a portion of the SGT10166 region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al. (1989) or Ausubel et al. (1992). Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding SGT10166 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding SGT10166 is present in a cell or tissue. The present invention includes all novel probes having at least 8 nucleotides derived from SEQ ID NO:1 or SEQ ID NO:3, its complement or functionally equivalent nucleic acid sequences. The present invention does not include probes which exist in the prior art. That is, the present invention includes all probes having at least 8 nucleotides derived from SEQ ID NO:1, with the proviso that they do not include probes existing in the prior art.

Similar considerations and nucleotide lengths are also applicable to primers which may be used for the amplification of all or part of the SGT10166 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding SGT10166 is present in a cell or tissue. The present invention includes all novel primers having at least 8 nucleotides derived from the SGT10166 locus for amplifying the SGT10166 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein purification" refers to various methods for the isolation of the SGT10166 polypeptides from other biological material, such as from cells transformed with recombinant nucleic acids encoding SGT10166, and are well known in the art. For example, such polypeptides may be purified by immunoaffinity chromatography employing, e.g., antibodies prepared against SGT10166 using conventional techniques. Various methods of protein purification are well known in the art, and include those described in Deutscher (1990) and Scopes (1982).

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A SGT10166 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to join together nucleic acid segments of desired functions to generate a desired combination of functions. Alternatively, it is performed to replace a codon with a redundant codon encoding the same or a conservative amino acid, while typically introducing or removing a sequence recognition site.

"Regulatory sequences" refers to those sequences normally within 100 kb of the coding region of a locus, but they may also be more distant from the coding region, or they may be located within introns of the gene, which affect the expression of the gene (including transcription of the gene, and translation, splicing, stability or the like of the messenger RNA).

"Substantial homology, similarity or identity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk A M, ed., Oxford University Press, New York, 1988; Biocomputing: Informatics and Genome Projects, Smith D W, ed., Academic Press, New York, 1993; Computer Analysis of Sequence Data, Part I, Griffin A M and Griffin H G, eds., Humana Press, New Jersey, 1994; Sequence Analysis in Molecular Biology, von Heinje G, Academic Press, 1987; and Sequence Analysis Primer, Gribskov M and Devereux J, eds., M Stockton Press, New York, 1991). Methods commonly employed to determine identity between two sequences include, but are not limited to those disclosed in *Guide to Huge Computers,* Martin J. Bishop, ed., Academic Press, San Diego, 1994, and Carillo and Lipman (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or (similarity or identity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa (1984). The length of homology comparison, as described, may be over longer stretches, and in certain embodiments will often be over a stretch of at least about nine nucleotides, usually at least about 20 nueleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson (1968).

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705, as well as the software described above with reference to nucleic acid homology. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type SGT10166 nucleic acid or wild-type SGT10166 polypeptide. The modified polypeptide will be substantially homologous to the wild-type SGT10166 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type SGT10166 polypeptide. Alternatively, the similarity of function (activity) of the modified polypeptide may be higher than the activity of the wild-type SGT10166 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type SGT10166 gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe, a primer or an antisense will form a stable hybrid under desired conditions.

The practice of the present invention employs, unless otherwise indicated, conventional techniques of chemistry, molecular biology, microbiology, recombinant DNA and genetics. See, e.g., Maniatis et al. (1982); Sambrook et al. (1989); Ausubel et al. (1992); Glover (1985); Anand (1992); Guthrie and Fink (1991); Weissbach and Weissbach (1986); Zaitlin et al. (1985) and Gelvin et al. (1990).

Methods of Use: Preparation of Recombinant or Chemically Synthesized Nucleic Acids; Vectors. Transformation. Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. Purification of nucleic acids produced by the methods of the present invention are described, e.g., in Sambrook et al. (1989) or Ausubel et al. (1992).

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al. (1989) or Ausubel et al. (1992).

An appropriate promoter and other necessary vector sequences will be selected so as to be functional in the host, and may include, when appropriate, those naturally associated with the SGT10166 gene. Examples of workable combinations of cell lines and expression vectors are described in Sambrook et al. (1989) or Ausubel et al. (1992); see also, e.g., Metzger et al. (1988). Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A.

Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). See also, e.g., U.S. Pat. Nos. 5,691,198; 5,735,500; 5,747,469 and 5,436,146. Plant control sequences are disclosed in, for example, U.S. Pat. Nos. 5,106,739; 5,322,938; 5,710,267; 5,268,526 and 5,290,294.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that (a) confer resistance to antibiotics or other toxic substances, e.g. ampicillin, neomycin, methotrexate, etc., (b) complement auxotrophic deficiencies, or (c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a viral genome); and other methods. See generally, Sambrook et al. (1989) and Ausubel et al. (1992). The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the SGT10166 nucleic acid or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of SGT10166 polypeptides.

The probes and primers based on the SGT10166 gene sequence disclosed herein are used to identify gene sequences and proteins homologous to SGT10166 in other species. These gene sequences and proteins are used in the diagnostic/prognostic, such as predicting reproductive phenotype in transgenic plants and genetic engineering methods described herein for the species from which they have been isolated.

Methods of Use: Controlling Reproductive Dehiscence

The vectors used to transform plant cells comprise an SGT10166 nucleic acid or homologous nucleic acid or portion thereof which is capable of hybridizing with the endogenous gene homologous to the SGT10166 gene of *Arabidopsis.* For purposes of description, the invention will be described with reference to the SGT10166 gene and SGT10166 protein. It is understood that such reference also includes homologous genes and proteins." Thus, such nucleic acids include the positive strand of the SGT10166 or homologous gene encoding all or part of a protein and the antisense strand. In either case, the SGT10166 or homologous nucleic acid or its transcript is capable of hybridizing with and endogenous gene as defined herein or its transcript. The conditions under which such hybridization occurs include the physiological or equivalent conditions found within plant cells including that found in the nucleus and cytoplasm as well as standard in vitro conditions normally used by the skilled artisan to determine sequence homology as between two nucleic acids. Such in vitro conditions range from moderate (about 5×SSC at 52° C.) to high (about 0.1×SSC at 65° C.) stringency conditions.

The SGT10166 or homologous gene is used to construct sense or antisense vectors for transforming plant cells. The construction of such vectors is facilitated by the use of a binary vector which is capable of manipulation and selection in both a plant and a convenient cloning host such as a prokaryote. Thus, such a binary vector can include a kanamycin or herbicide resistance gene for selection in plant cells and an actinomycin resistance gene for selection in a bacterial host. Such vectors, of course, also contain an origin of replication appropriate for the prokaryotic host used, and preferably at least one unique restriction site or a polylinker containing unique restriction sites to facilitate vector construction.

In one embodiment, a constitutive promoter is used to drive expression of the SGT10166 nucleic acid within at least a portion of the reproductive tissues in the recipient plant. A particularly preferred promoter is the cauliflower mosaic virus 35S transcript promoter (Guilley et al., 1982; Odell et al., 1985; and Saunders et al., 1987). However, other constitutive promoters can be used, such as the $\alpha$-1 and $\beta$-1 tubulin promoters (Silflow et al., 1987) and the histone promoters (Chaubet et al., 1987). Tissue specific promoters can also be used. For example, the "endogenous" promoter of the SGT10166 gene may be used to drive expression of antisense or dominant negative transgenes in the region where the wild type gene is expressed.

In a further embodiment of the invention, the vector used to transform the plant cell to produce a plant having an altered dehiscence phenotype is constructed to target the insertion of the SGT10166 or homologous nucleic acid into an endogenous promoter within a plant cell. One type of vector which can be used to target the integration of an SGT10166 or homologous nucleic acid to an endogenous promoter comprises a positive-negative selection vector analogous to that set forth by Monsour et al. (1988), which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it (Kempin et al., 1997). When such an approach is used, it is preferred that a replacement-type vector be used to minimize the likelihood of reversion to the wild-type phenotype.

The vectors of the invention are designed such that the promoter sequence contained in the vector or the promoter sequence targeted in the plant cell genome are operably linked to the nucleic acid encoding the SGT10166 or homologous gene. When the positive strand of the SGT10166 gene or homologous gene is used to express all or part of the SGT10166 protein, the term "operably linked" means that the promoter sequence is positioned relative to the coding sequence of the agamous nucleic acid such that RNA polymerase is capable of initiating transcription of the SGT10166 nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into SGT10166 protein. When an antisense orientation of the SGT10166 nucleic acid is used, all that is required is that the promoter be operably linked to transcribe the SGT10166 antisense strand. Thus, in such embodiments, only transcription start and termination sequences are needed to provide an RNA transcript capable of hybridizing with the mRNA or other RNA transcript from the endogenous SGT10166 gene. In addition to promoters, other expression regulation sequences, such as enhancers, can be added to the vector to facilitate the expression of SGT10166 nucleic acid in vivo.

Once a vector is constructed, the transformation of plants can be carried out in accordance with the invention by essentially any of the various transformation methods known to those skilled in the art of plant molecular biology. Such methods are generally described in Wu and Grossman (1987). As used herein, the term "transformation" means the alteration of the genotype of a plant cell by the introduction of a nucleic acid sequence. Particular methods for transformation of plant cells include the direct microinjection of the nucleic acid into a plant cell by use of micropipettes. Alternatively, the nucleic acid can be transferred into a plant cell by using polyethylene glycol (Paszkowski et al., 1984). Other transformation methods include electroporation of protoplasts (Fromm et al., 1985); infection with a plant specific virus, e.g., cauliflower mosaic virus (Hohn et al., 1982) or use of transformation sequences from plant specific bacteria such as Agrobacterium tumefaciens, e.g., a Ti plasmid transmitted to a plant cell upon infection by *Agrobacterium tumefaciens* (Horsch et al., 1984; Fraley et al., 1983). Alternatively, plant cells can be transformed by introduction of nucleic acid contained within the matrix or on the surface of small beads or particles by way of high velocity ballistic penetration of the plant cell (Klein et al., 1987). The nucleic acid introduced with ballistics may be a chimeric oligonucleotide designed to target a small number of mutated bases to a selected segment of the endogenous SGT10166 gene or homologous gene (Beetham et al., 1999). A small number of mutated bases can also be introduced into a selected segment of the endogenous SGT10166 gene using homologous recombination (Kempin et al., 1997).

After the vector is introduced into a plant cell, selection for successful transformation is typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. (1983); and H. Binding (1985). When transformation is of an organ part, regeneration can be from the plant callus, explants, organs or parts. Such methods for regeneration are also known to those skilled in the art. See, e.g., Wu and Grossman (1987); Weissbach and Weissbach (1986); and Klee et al. (1987).

Once plants have been regenerated, one or more plants are selected based upon a change in the dehiscence phenotype. Such selection can be by visual observation of gross morphological changes in fruit structure, e.g., failure of the seed pod to open, by observation in a change in inflorescence or by observation in changes in microscopic fruit structure, e.g., by electron microscopy and the like.

In those cases wherein a dominant phenotype is conferred upon transformation with a vector containing an SGT10166 nucleic acid, the alteration in dehiscence may possible result in a sterile plant. In such cases, the plant can be propagated asexually by the taking of cuttings or by tissue culture techniques to produce multiple identical plants. Alternatively, the alteration in dehiscence can be ablated when desired as further described herein.

When the transformed plant is characterized by a recessive phenotype, e.g., when an antisense construct is used which is insufficient to confer the desired phenotype or which confers an intermediate phenotype which does not result in a indehiscence exhibiting plant, such transformed plants can be inbred to homozygosity to obtain the desired phenotype. Such plants may then be asexually propagated or the alteration in dehiscence can be ablated when desired as further described herein.

Either antisense or co-suppression mechanisms using SGT10166 nucleic acids can result in altered dehiscence. Plants having such modified dehiscence phenotypes can be used as model systems for further study of the formation and differentiation of fruit tissue in plants.

Methods of Use: Regulatory Sequences for Plant Transformation

In another aspect of the invention, a DNA molecule is provided which comprises regulatory sequences of the SGT10166 gene operably linked to one or more genes or antisense DNA. The entire genomic sequence for *Arabidopsis* has been cloned and determined. On the basis of the genomic sequence for SGT10166 disclosed herein, the promoter and/or enhancer and/or termination sequences can be readily determined by examining the genomic sequences in GenBank. The regulatory sequences may be the SGT10166 promoter, intron sequences or termination sequences. The SGT10166 promoter begins at the start of exon 1 in SEQ ID NO:3 and extends upstream by about 2 kb of sequence. At least one regulatory sequence is found in intron 1. The gene or antisense DNA imparts an agronomically useful trait or selectable marker to a transformed plant. In one embodiment, the DNA molecule include the SGT10166 promoter and an additional nucleotide sequence that influences gene expression. Examples of nucleotide sequences that influence the regulation of heterologous genes include enhancers or activating regions, such as those derived from CaMV 35S, opine synthase genes or other plant genes (U.S. Pat. Nos. 5,106,739; 5,322,938; 5,710,267; 5,268,526; 5,290,294). In a second embodiment, a promoter such as CaMV 35S promoter is used with regulatory sequences, such as intron sequences or termination sequences of SGT10166. In a third embodiment, an intron of SGT10166 is inserted into a DNA molecule which will be used to transform plants as a means to easily select or identify transformed tissue in the presence of transforming bacteria. In a fourth embodiment, the DNA molecule is part of an expression vector. In a fifth embodiment, the DNA molecule is part of a transformation vector.

In an additional aspect of the present invention, transformed plant cells and tissues, transformed plants and seeds of transformed plants are provided. The expression of the gene or antisense DNA is regulated by the SGT10166 regulatory sequences and additional regulatory sequences, if present.

By means of the present invention, agronomic genes and selectable marker genes can be operably linked to SGT10166 regulatory sequences and expressed in transformed plants. More particularly, plants can be genetically engineered to express various phenotypes of agronomic interest. Such genes included, but are not limited to, those described herein.

1. Genes That Confer Resistance or Tolerance to Pests or Disease (A) Plant disease resistance genes. Plant defenses are often activated by specific interaction between the product of a disease resistance (R) gene in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al., 1994), the tomato Pto gene, which encodes a protein kinase, for resistance to *Pseudomonas syringae* pv. tomato (Martin et al., 1993), and the *Arabidopsis* RSSP2 gene for resistance to *Pseudomonas syringae* (Mindrinos et al., 1994).

(B). A *Bacillus thuringiensis* protein, a derivative thereof or a synthetic polypeptide modeled thereon, such as, a nucleotide sequence of a Bt δ-endotoxin gene (Geiser et al., 1986). Moreover, DNA molecules encoding δ-endotoxin genes can be purchased from American Type Culture Collection (Rockville, Md.), under ATCC accession numbers. 40098, 67136, 31995 and 31998.

(C) A lectin, such as nucleotide sequences of several *Clivia miniata* mannose-binding lectin genes (Van Damme et al., 1994).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987), a tobacco proteinase inhibitor I (Huub et al., 1993), and an α-amylase inhibitor (Sumitani et al., 1993).

(F) An insect-specific peptide or neuropeptide which, upon expression, disrupts the physiology of the affected pest. Examples of such genes include, an insect diuretic hormone receptor (Reagan, 1994), an allostatin identified in *Diploptera puntata* (Pratt, 1989), insect-specific paralytic neurotoxins (U.S. Pat. No. 5,266,361).

(G) An insect-specific venom produced in nature by a snake, a wasp, etc., such as, a scorpion insectotoxic peptide (Pang, 1992).

(H) An enzyme responsible for a hyperaccumulation of a monoterpene, a sesquiterpene, a steroid, hydroxamic acid, a phenylpropanoid derivative or another non-protein molecule with insecticidal activity.

(I) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylasc, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993) and parsley ubi4-2 polyubiquitin gene (Kawalleck et al., 1993).

(J) A molecule that stimulates signal transduction. Examples of such molecules include, nucleotide sequences for mung bean calmodulin cDNA clones (Botella et al., 1994), a nucleotide sequence of a maize calmodulin cDNA clone (Griess et al., 1994).

(K) A hydrophobic moment peptide. See U.S. Pat. Nos. 5,659,026 and 5,607,914, the latter teaches synthetic antimicrobial peptides that confer disease resistance.

(L) A membrane permease, a channel former or a channel blocker, such as, a cecropin-β lytic peptide analog (Jaynes et al., 1993) which renders transgenic tobacco plants resistant to *Pseudomonas solanacearum*.

(M) A viral protein or a complex polypeptide derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990).

(N) An insect-specific antibody or an immunotoxin derived therefrom. Thus, an antibody targeted to a critical metabolic function in the insect gut would inactivate an affected enzyme, killing the insect. For example, Taylor et al. (1994) shows enzymatic inactivation in transgenic tobacco via production of single-chain antibody fragments.

(O) A virus-specific antibody. See, for example, Tavladoraki et al. (1993), which shows that transgenic plants expressing recombinant antibody genes are protected from virus attack.

(P) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992). The cloning and characterization of a gene which encodes a bean endopolygalacturonase-inhibiting protein is described by Toubart et al. (1992).

(Q) A developmental-arrestive protein produced in nature by a plant, such as the barley ribosome-inactivating gene, have increased resistance to fungal disease (Longemann et al., 1992).

2. Genes That Confer Resistance or Tolerance to a Herbicide (A) A herbicide that inhibits the growing point or meristem, such as an imidazalinone or a sulfonylurea. Exemplary genes in this category code for mutant ALS (Lee et al., 1988) and AHAS enzyme (Miki et al., 1990).

(B) Glyphosate (resistance imparted by mutant EPSP synthase and aroA genes) and other phosphono compounds such as glufosinate (PAT and bar genes), and pyridinoxy or phenoxy propionic acids and cyclohexones (ACCase inhibitor encoding genes). See, for example, U.S. Pat. No. 4,940,835, which discloses the nucleotide sequence of a form of EPSP synthase which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthase genes which confer resistance to herbicides such as L-phosphinothricin. The nucleotide sequence of a phosphinothricin acetyltransferase gene is provided in European application No. 0 242 246. De Greef et al. (1989) describes the production of transgenic plants that express chimeric bar genes coding for phosphinothricin acetyltransferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al. (1992).

(C) A herbicide that inhibits photosynthesis, such as a triazine (psbA and GST genes) and a benzonitrile (nitrilase gene). Przibilla et al. (1991) describes the use of plasmids encoding mutant psbA genes to transform Chlamydomonas. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a GST (glutathione S-transferase) is described by Hayes et al. (1992).

3. Genes That Confer Resistance or Tolerance to Environmental Stresses (A) Cold, freezing or frost. This includes genes that code for proteins that protect from freezing and for enzymes that synthesize cryoprotective solutes. Examples of such genes are Arabidopsis COR15α (Artus et al., 1996) and spinach CAP160 (Kaye et al., 1998). Also in this category are regulatory genes that control the activity of other cold tolerance genes (PCT International Publication Number WO 98/09521).

(B) Drought or water stress. Kasuga et al. (1999) report how stress inducible expression of DREBIA in transgenic plants increases their tolerance of drought stress. Pilon-Smits et al. (1998) report that expression of bacterial genes for synthesis of trehalose produces tolerance of water stress in transgenic tobacco.

(C) Salinity or salt stress. Genes that code for proteins that minimize uptake of sodium in the presence of high salt, or cause the plant to sequester sodium in vacuoles, can enable plants to tolerate higher levels of salt in the soil. The wheat HKTI potassium transporter, described by Rubio et al. (1999), is an example of the former. Apse et al. (1999) describe how an Arabidopsis $Na^+/H^+$ antiporter can act in the latter manner.

(D) Metals. Protection from the toxic effects of metals such as aluminum and cadmium can be accomplished by transgenic expression of genes that prevent uptake of the metal, or that code for chelating agents that bind the metal ions to prevent them from having a toxic effect. Examples of such genes are Arabidopsis ALR104 and ALR108 (Larsen et al., 1998) and genes for the enzymes involved in phytochelatin synthesis (Schafer et al., 1998).

4. Genes That Confer or Contribute to a Value-Added Trait (A) Modified fatty acid metabolism, for example, by transforming maize or Brassica with an antisense gene or stearoyl-ACP desaturase to increase stearic acid content of the plant (Knutzon et al., 1992).

(B) Decreased phytate content (1) Introduction of a phytase-encoding gene would enhance breakdown of phytate, adding more free phosphate to the transformed plant, such as the Aspergillus niger phytase gene (Van Hartingsveldt et al., 1993).

(2) A gene could be introduced that reduces phytate content. In maize, for example, this could be accomplished by cloning and then reintroducing DNA associated with the single allele which is responsible for maize mutants characterized by low levels of phytic acid (Raboy et al., 1990).

(C) Modified carbohydrate composition effected, for example, by transforming plants with a gene coding for an enzyme that alters the branching pattern of starch. Examples of such enzymes include, Streptococcus mucus fructosyltransferase gene (Shiroza et al., 1988), Bacillus subtilis levansucrase gene (Steinmetz et al., 1985), Bacillus lichenformis α-amylase (Pen et al., 1992), tomato invertase genes (Elliot et al., 1993), barley amylase gene (Søgaard et al., 1993), and maize endosperm starch branching enzyme II (Fisher et al., 1993).

(D) Modified lignin content. The amount or composition of lignin can be altered by increasing or decreasing expression of the biosynthetic enzymes for phenylpropanoid lignin precursors, such as cinnamyl alcohol dehydrogenase (CAD), 4-coumarate:CoA ligase (4CL), and O-methyl transferase (OMT). These and other genes involved in formation of lignin are described in U.S. Pat. No. 5,850,020.

5. Selectable Marker Genes (A) Numerous selectable marker genes are available for use in plant transformation including, but not limited to, neomycin phosphotransferase II, hygromycin phosphotransferase, EPSP synthase and dihydropteroate synthase. See, Miki et al. (1993).

Synthesis of genes suitably employed in the present invention can be effected by means of mutually priming long oligonucleotides. See, for example, Ausubel et al. (1990) and Wosnick et al. (1987). Moreover, current techniques which employ the polymerase chain reaction permit the synthesis of genes as large as 6 kilobases in length or longer. See Adang et al. (1993) and Bambot et al. (1993). In addition, genes can readily be synthesized by conventional automated techniques.

EXAMPLES

The present invention is further described in the following examples, which are offered by way of illustration and are not intended to limit the invention in any manner. Standard techniques well known in the art or the techniques specifically described below are utilized.

Example 1

Isolation and Mutation Phenotype

Using transposon-mediated gene trap mutagenesis approach, we isolated a mutation that blocks the process of silique dehiscence (Sundaresan et al., 1995).

Figure 2:
FIG. 2 depicts the GUS expression pattern of SGT10166 in developing silique, in the order of increasing age (left to right).

The SGT10166 mutation was isolated from a collection of independent insertion lines generated using a gene trap Ds transposable element. The two-element transposon system utilizes a maize Ac-Ds transposon and the reporter gene GUS (Sundaresan et al., 1995). In the gene trap insertion line SGT10166, the SGT10166 mutant was identified in the F3 progeny of a gene trap line where the siliques displayed an indehiscent phenotype (FIG. 2). The valves failed to separate from the replum, and the seeds could be harvested only if the fruit was opened manually. Apart from the indehiscent phenotype, the plant appeared normal.

Example 2

GUS Expression Pattern

Figures 3A, 3B:
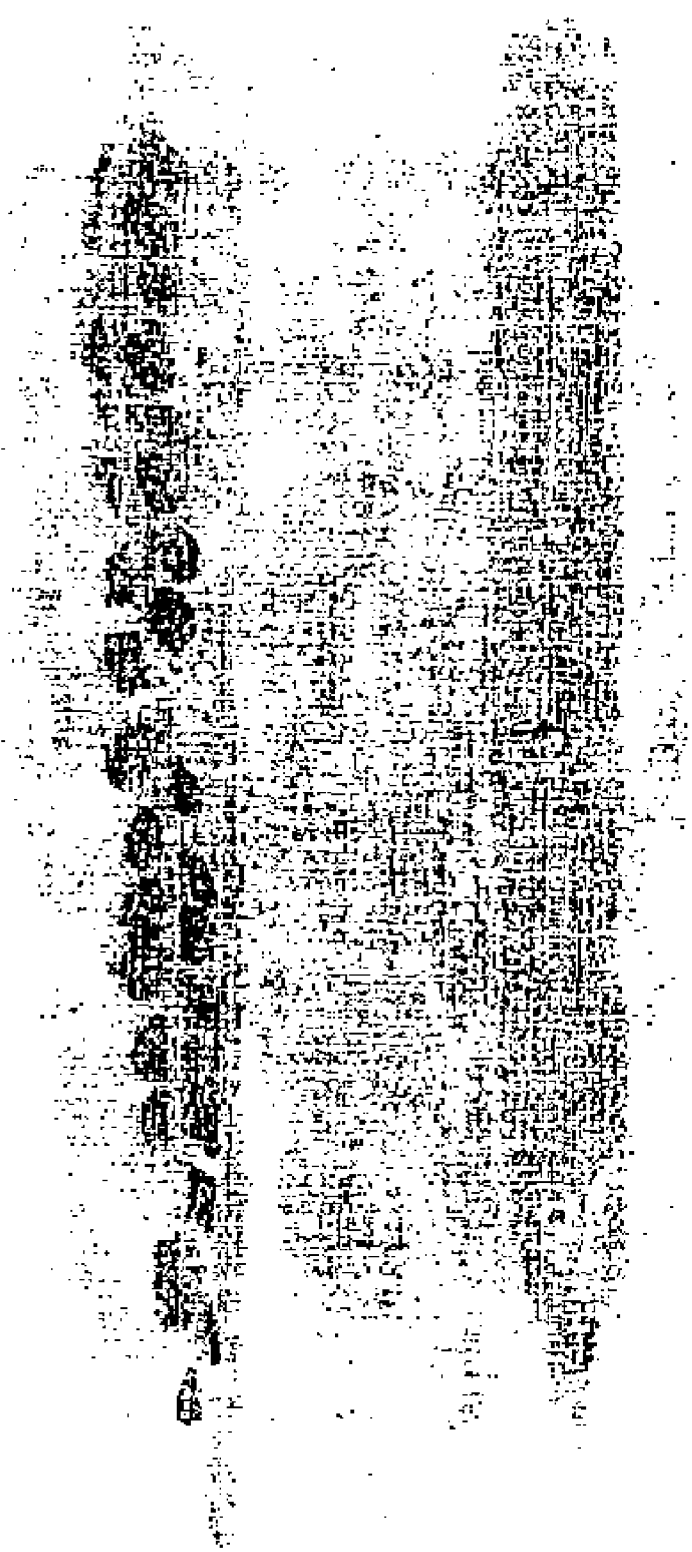
FIG. 3 depicts the indehiscent phenotype of SGT10166, where (a) is the mature wild type silique, and (b) is the mature SGT10166 silique.

The Ds gene trap element insertion confers GUS reporter gene expression, hence it was possible to analyze the endogenous expression pattern of the gene by histochemical staining for GUS activity (See, Sundaresan et al., 1995). Gus expression commences in young buds at the tip of the gynoecium cylinder. Later, as it develops, the expression expands into the stigmatic papillae and the distal portion of the gynoecium. In mature flowers the whole gynoecium stains. After fertilization, in the silique, the expression was limited to the valve replum boundary being more intense at the distal and proximal part of the valve (FIG. 3).

Example 3

Gene Analysis

To understand the nature of the defect that causes an indehiscent phenotype, further characterization of the gene was performed. Through Tail PCR, a fragment of genomic DNA flanking the Ds element was amplified (Parinov et al., 1999). A search of the *Arabidopsis thaliana* genomic database revealed that the flanking sequences were identical to the genomic sequences from chromosome 5, contained within BAC clone accession number AB020742. Gene specific primers were designed to amplify a portion of cDNA sequence from an *Arabidopsis thaliana* flower cDNA library (The cDNA clones were isolated from an *Arabidopsis thaliana* flower cDNA library, prepared from the ecotype Landsberg erecta. The cDNA library is available from the *Arabidopsis* Stock Center ABRC at Ohio State University, and had been constructed using the Stratagene Uni-ZAP XR vector system (Weigel et al., 1992). The library was screened according to the manufacturer's protocol). The PCR fragment was then used as a probe to screen the same library. The cDNA clone isolated from the screen was a length of 931 base pairs and is predicted to encode a 210 amino acid protein. Analysis of the cDNA sequence revealed a strong similarity between SGT10166 and proteins belonging to the basic helix loop helix (bHLH) class of transcription factors. Members of the bHLH family of proteins play an important role in transcriptional regulation in animals, plants and fungi. These proteins generally function as dimers with the HLH region being involved in the homo/heterodimerization process and the basic domains functions to bind the DNA. In plants, many bHLH domain proteins have been identified and implicated in different functions (Murre et al., 1989). For example, bHLH proteins regulate anthocyanin biosynthesis in maize (B-Peru and R/Lc genes) (Radicella et al., 1991; Ludwig et al., 1989), response to abscisic acid and dehydration in *Arabidopsis* (rd 22 BPI) (Abe et al., 1997), and the expression of seed storage proteins in *Phaseolus* (PG1) (Kawagoe and Murai, 1996).

The genomic sequence with exons and introns for SGT10166 is set forth in SEQ ID NO:3. The sequences for SEQ ID NO:3 are set forth in Table No. 1.

TABLE 1

Exons and Introns of the SGT10166 Gene

| Exon/Intron | 5' Nucleotide | 3' Nucleotide |
|---|---|---|
| Exon 1 | 1007 (start codon) | 1243 |
| Intron 1 | 1244 | 1355 |
| Exon 2 | 1356 | 1427 |
| Intron 2 | 1428 | 1517 |
| Exon 3 | 1518 | 1583 |
| Intron 3 | 1584 | 1661 |
| Exon 4 | 1662 | 1727 |
| Intron 4 | 1728 | 1821 |
| Exon 5 | 1822 | 2013 (stop codon) |

Example 4

Reversion Analysis

To confirm that the observed phenotype seen in SGT10166 was caused by the insertion of the Ds element, reversion analysis was performed (Yang et al., 1999). DNA sequencing of the Ds insertion site revealed that the Ds insertion had not resulted in a typical 8 bp target site duplication. The base pair changes present at the Ds insertion site are shown in FIG. 5. The wildtype ALC sequence shown in FIG. 5 (SEQ ID NO:8) corresponds to bases 331–352 of SEQ ID NO:1. The tagged site is shown as SEQ ID NOs:9 and 10 which are interrupted by the insert Ds was remobilized by crossing to plants carrying the Ac transposase gene (Sundaresan et al., 1995) and eight mutant plants were observed with revertant wild type sectors, that is, they had siliques which dehisced. Seeds from these revertants siliques were planted, DNA prepared and the sequence alterations expected from Ds excision were analyzed. All sequenced revertant genes contained an excised Ds element as evidenced by the absence of Ds sequences, and a 9 bp footprint at the same site. The footprint restores the reading frame and results in the addition of three extra amino acids to the original protein (FIG. 5, bolded 9 bases of SEQ ID NO:11 shown as the revertant). This result confirms that mutation was caused by the insertion of the Ds in the SGT10166 locus. In addition a stable allele with a 10 bp footprint which does not restore the reading frame was also isolated and was designated as alc10 (FIG. 5; SEQ ID NO:12). The alc10 plants remained indehiscent as expected.

Example 5

Complementation Studies

To prove that the isolated cDNA sequence of SGT10166 is sufficient to confer dehiscence, we introduced the presumptive full length cDNA clone of SGT10166 under the control of CaMV 35S promoter into the mutant plants by *Agrobacterium* mediated transformation (Clough and Bent, 1998). Out of 15 independent transformants obtained, dehiscence was restored completely in 2 mutant plants. These results show that the sequence isolated is necessary and sufficient for fruit dehiscence.

Example 6

Dominant Negative Studies

Since SGT10166 gene encodes a myc-related bHLH domain protein, it is possible to make dominant negative regulators against it to alter the dehiscence process. As previously proposed in the application, we made such a dominant negative construct by deleting the basic domain of the SGT10166 gene and replacing it with acidic sequences (Krylov et al., 1997). Such a protein should act as a dominant negative regulator by sequestering the endogenous SGT10166 bHLH protein to form inactive dimers. This construct was made by deleting bases 290–340 of SEQ ID NO:1 (shown as SEQ ID NO:13) and replacing them with SEQ ID NO:14 to yield SEQ ID NO:15 which encodes SEQ ID NO:16. This construct was transformed into wild type *Arabidopsis* plants by *Agrobacterium* mediated transformation (Clough and Bent, 1998). We were able to delay dehiscence considerably by up to two weeks in 2 out of 35 independent transformants obtained. This result could also be explained as the result of co-suppression mechanisms rather than the proposed dominant negative effects. Nevertheless, we have established that the SGT10166 gene can be used in transgenic plants to delay dehiscence. It should be similarly possible to engineer indehiscent or delayed dehiscence plants by reducing the activity of this gene using an anti-sense approach (Gray et al., 1992).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Abe K, et al. (1987). *J. Biol Chem.* 262:16793–16797.
Abe H, et al. (1997). *The Plant Cell* 9:1859–1868.
Adang M J, et al. (1993). *Plant Molec. Biol.* 21:11311145.
Anand R (1992). *Techniques for the Analysis of Complex Genomes*, (Academic Press).
Altschul S F, et al. (1990). *J Mol. Biol* 215:403–410.
Altschul S F, et al. (1997). *Nucl. Acids Res.* 25:3389–3402.
Apse M P, et al. (1999). *Science* 285:1256–1258.
Ausubel F M, et al. (1992). *Current Protocols in Molecular Biology*, (John Wiley & Sons, New York, N.Y.).
Bambot S B, et al.(1993). *PCR Methods and Applications* 2:266–271.
Beachy et al. (1990). *Ann. Rev. Phytopathol* 28:451.
Beaucage S L and Caruthers M H (1981). *Tetra. Letts.* 22:1859–1862.
Beetham P R (1999). *Proc. Natl. Acad. Sci USA* 96:8774–8778.
Biocomputing: Informatics and Genome Projects, Smith D W, ed., Academic Press, NY (1993).
Botella J R, et al. (1994). *Plant Molec. Biol.* 24:757–766.
Carillo H and Lipman D (1988). *SIAM J. Applied Math.* 48:1073.
Chaubet et al. (1987). *Devel. Genet.* 8:461–473.
Clough S J and Bent A F (1998). *Plant J.* 16:735–743.
Compton J (1991). *Nature* 350:91–92.
*Computational Molecular Biology*, Lesk A M, ed., Oxford Univ. Press, NY (1988).
*Computer Analysis of Sequence Data*, Part I, Griffin A M and Griffin H G, eds., Humana Press, NJ (1994).
Coupe S A, et al. (I 994). *Plant Molecular Biology* 24:223–227.
DeGreef, et al. (1989). *Bio/Technology* 7:61.
Deutscher M (1990). *Meth. Enzymology* 182:83–89 (Academic Press, San Diego, Calif.).
Elliot, et al. (1993). *Plant Molec. Biol.* 21:515.
*Enhancers and Eukaryotic Gene Expression*, Cold Spring Harbor Laboratory, Cold Spring Harbor, N.Y. (1983).
Evans, et al. (1983). *Protoplasts Isolation and Culture, Handbook of Plant Cell Cultures* 1: 124–176 (MacMillan Publishing Co., NY).
Fahy E, et al. (1991). *PCR Methods Appl.* 1:25–33.
Fiers W, et al. (1978). *Nature* 273:113–120.
Fisher D K, et al. (1993). *Plant Physiol.* 102:1045–1046.
Fraley R T, et al. (1983). *Proc. Nat. Acad Sci USA* 80:4803–4807.
Fromm M, et al. (1985). *Proc. Nat. Acad Sci. USA* 82:5824–5828.
Geiser M, et al. (1986). *Gene* 48:109–118.
Gelvin S, et al. (eds.) (1990). *Plant Molecular Biology: Manual*, Kluwer Academic Press, Dordrecht, Netherlands
Glover D (1985). *DNA Cloning*, I and II (Oxford Press).
Gray J, et al. (1992). *Plant Mol Bio.* 19 (1): 69–87.
Griess E A, et al. (1994). *Plant Physiol.* 104:1467–1468.
Gu Q, et al. (1998). *Development* 125:1509.
*Guide to Huge Computers*, Martin J. Bishop, ed., Academic Press, San Diego, Calif. (1994).
Guilley H, et al. (1982). *Cell* 30:763–773 (1982).
Guthrie G and Fink G R (1991). *Guide to Yeast Genetics and Molecular Biology* (Academic Press).
Hayes J D, et al. (1992). *Biochem. J.* 285:173–180.
Hohn et al. (1982). *Molecular Biology of Plant Tumors* (Academic Press, NY), pp. 549–560.
Horsch et al. (1984). *Science* 233:496–498.
Huub et al. (1993). *Plant Molec. Biol.* 21:985.
Innis M A, et al. (1990). *PCR Protocols: A Guide to Methods and Applications* (Academic Press, San Diego, Calif.).
Jakoby W B and Pastan I H (eds.) (1979). *Cell Culture. Methods in Enzymology* Vol. 58 (Academic Press, Inc., Harcourt Brace Jovanovich (NY)).
Jaynes, et al. (1993). *Plant Sci.* 89:43.
Jones D A, et al. (1994). *Science* 266:789–793.
Kanchisa M (1984). *Nucl Acids Res.* 12:203–213.
Kasuga M, et al. (1999). *Nature Biotech.* 17:287–291.
Kawagoe Y and Murai N (1996). *Plant Sci.* 116:47.
Kawalleck P, et al. (1993). *Plant Mol. Biol* 21:673–684.
Kaye C, et al. (1998). *Plant Physiol.* 116:1367–1377.
Kempin S A, et al. (1997). *Nature* 389:802–803.
Klee, et al. (1987). *Ann. Review of Plant Physiology* 38:467–486.

Klein et al. (1987). *Nature* 327:70–73.
Knutzon D S, et al. (1992). *Proc. Nat. Acad. Sci. USA* 89:2624–2628.
Kramer K J, et al. (1993). *Insect Biochem. Mol. Biol.* 23:691–701.
Krylov D, et al. (1997). *Proc. Natl. Acad Sci. USA* 94:12274–12279.
Kubo T, et al. (1988). *FEBS Lett.* 241:119–125.
Kyte J and Doolittle R F (1982). *J. Mol. Biol.* 157:105–132.
Lamb C J, et al. (1992). *Bio/Technology* 10:1436–1445.
Larsen P B, et al. (1998). *Plant Physiol.* 117: 9–18.
Longemann, et al. (1992). *Bio/Technology* 10:3305.
Ludwig S R, et al. (1989). *Proc. Natl. Acad. Sci. USA* 86:7092–7096.
Maniatis T, et al. (1982). *Molecular Cloning: A Laboratory Manual* (Cold Spring Harbor Laboratory, Cold Spring Harbor, N.Y.).
Marshall, et al. (1992). *Theor. Appl. Genet.* 83:435.
Martin G B, et al. (1993). *Science* 262:1432–1436.
Matteucci M D and Caruthers M H (1981). *J. Am. Chem. Soc.* 103:3185.
Metzger D, et al. (1988). *Nature* 334:31–36.
Miki, et al. (1990). *Theor. Appl. Genet.* 80:449.
Miki, et al. (1993). "Procedures for Introducing Foreign DNA into Plants," in *Methods in Plant Molecular Biology and Biotechnology*, Glick et al. (eds.), CRC Press, pp. 67–88.
Mindrinos M, et al. (1994). *Cell* 78:1089–1099.
Mol JMN, et al. (1994). Post-transcriptional inhibition of gene expression: sense and antisense genes. In: J. Paszkowski (Ed.). *Homologous Recombination and Gene Silencing in Plants*. Kluwer Academic Publishers. Dordrecht, Netherlands. pp. 309–334.
Monsour, et al. (1988). *Nature* 336:348–352.
Murre C, et al. (1989). *Cell* 56:777–783.
Odell J T, et al. (1985). *Nature* 313:810–812.
Pang, et al. (1992). *Gene* 116:165.
Parinov S, et al. (1999). *The Plant Cell* 11:2263–2270.
Pen J, et al. (1992). *Bio/Technology* 10:292–296.
Pilon-Smits EAH, et al. (1998). *J. Plant Physiol.* 152: 525–532.
Przibilla E, et al. (1991). *Plant Cell* 3:169–174.
Raboy, et al. (1990). *Maydica* 35:383.
Radicella J P, et al. (1991). *Plant Mol. Biol.* 17:127–130.
Reagan J D (1994). *J. Biol. Chem.* 269:9–12.
Sambrook J, et al. (1989). *Molecular Cloning: A Laboratory Manual,* 2nd Ed. (Cold Spring Harbor Laboratory, Cold Spring Harbor, N.Y.).
Schafer H E, et al. (1998). *Plant Mol. Biol.* 37:87–97.
Scharf S J, et al. (1986). *Science* 233:1076–1078.
Scopes R (1982). *Protein Purification: Principles and Practice,* (Springer-Verlag, NY).
*Sequence Analysis in Molecular Biology,* von Heinje G, Academic Press (1987).
*Sequence Analysis Primer,* Gribskov M and Devereux J, eds., M Stockton Press, NY (1991)
*Sequence Analysis Software Package of the Genetics Computer Group,* Univ. of Wisconsin Biotechnology Center, Madison, Wis.
Sessions A (1999). *Trends Plant Sci.* 4:296–297.
Shiroza T, et al. (1988). *J. Bacterial* 170:810–816.
Silflow, et al. (1987). *Devel. Genet.* 8:435–460.
Søgaard M, et al. (1993). *J. Biol Chem.* 268:22480–22484.
Spargo C A, et al. (1996). *Mol. Cell. Probes* 10:247–256.
Steinmetz M, et al. (1985). *Mol. Gen. Genet.* 200:220–228.
Sumitani J, et al. (1993). *Biosci. Biotechnol Biochem.* 57:1243–1248.
Sundaresan V, et al. (1995). *Gene Dev.* 9:1797–1810.
Tavladoraki P, et al. (1993). *Nature* 366:469–472.
Taylor L P and Jorgensen R A (1992). *J. Hered.* 83:11–17.
Taylor et al. (1994). Abstract #497, Seventh Int'l. Symposium on Molecular Plant-Microbe Interactions.
Toubart P, et al. (1992). *Plant J.* 2:367–373.
Van Damme E J, et al. (1994). *Plant Mol Biol.* 24:825–830.
Van Hartingsveldt W, et al. (1993). *Gene* 127:87–94.
Walker G T, et al. (1992). *Nucl Acids Res.* 20:1691–1696.
Weissbach A and Weissbach H (eds.) 1986. *Methods in Enzymology,* Volume 118, Academic Press, Inc., Orlando, Fla.
Wetmur J G and Davidson N (1968). *J. Mol. Biol.* 31:349–370.
Weigel D, et al. (1992). *Cell* 69:843–859.
Wosnick M A, et al. (1987). *Gene* 60:115–127.
Wu D Y and Wallace R B (1989). *Genomics* 4:560–569.
Wu and Grossman (1987). *Methods in Enzymology,* Vol. 153, "Recombinant DNA Part D". Academic Press, NY.
Yang W C, et al. (1999). *Genes and Dev.* 13:2108–2117.
Zaitlin M, et al. (eds.) (1985). *Biotechnology in Plant Science,* Academic Press, Inc., Orlando, Fla.

Patents and Patent Applications:

Hitzeman et al., EP 73,675A.
European application No. 0 242 246
European patent application No. 0 333 033
PCT Publication Number WO 90/12084
PCT Publication Number WO93/02197
PCT Publication Number WO 98/09521.
U.S. Pat. No. 4,554,101.
U.S. Pat. No. 4,683,195.
U.S. Pat. No. 4,683,202.
U.S. Pat. No. 4,769,061.
U.S. Pat. No. 4,810,648
U.S. Pat. No. 4,940,835
U.S. Pat. No. 4,975,374
U.S. Pat. No. 5,106,739.
U.S. Pat. No. 5,266,361.
U.S. Pat. No. 5,268,526.
U.S. Pat. No. 5,270,184.
U.S. Pat. No. 5,290,294.
U.S. Pat. No. 5,322,938.
U.S. Pat. No. 5,409,818.
U.S. Pat. No. 5,436,146.
U.S. Pat. No. 5,455,166.
U.S. Pat. No. 5,607,914.
U.S. Pat. No. 5,633,441.
U.S. Pat. No. 5,659,026.
U.S. Pat. No. 5,691,198.
U.S. Pat. No. 5,710,267.
U.S. Pat. No. 5,735,500.
U.S. Pat. No. 5,747,469.
U.S. Pat. No. 5,850,020.

What is claimed is:

1. An isolated DNA molecule which encodes a mutated SGT10166 protein having the sequence of SEQ ID NO:16 wherein said mutated SGT10166 protein causes an indehiscent phenotype in a mature fruit.

2. The isolated DNA molecule of claim 1 comprising the nucleotide sequence of SEQ ID NO:15.

3. An isolated DNA molecule of comprising a dominant negative DNA construct comprising SEQ ID NO:1 with bases 290–340 replaced with SEQ ID NO:14.

4. The isolated DNA molecule of claim 1, which further comprises a heterologous promoter.

5. A transformed plant cell comprising the isolated DNA molecule of claim 1.

6. A transformed plant with altered dehiscence comprising the isolated DNA molecule of claim 1.

7. The transformed plant of claim 6, wherein said transformed plant produces seed pods.

8. A method for producing an indehiscent transgenic plant comprising transforming cells of said plant with the isolated DNA molecule of claim 1, selecting transformed plant cells containing said isolated DNA molecule and regenerating said indehiscent transgenic plant from said transformed plant cells.

9. A transformed plant comprising an isolated DNA molecule which encodes a mutated SGT10166 protein having the sequence of SEQ ID NO:16, wherein said transformed plant further comprises an inducible promoter which is operably linked to said isolated DNA molecule.

10. An isolated DNA molecule comprising the nucleotide sequence of SEQ ID NO: 3.

* * * * *